United States Patent [19]

Diamond et al.

[11] 4,147,804

[45] Apr. 3, 1979

[54] AMIDINOUREA LOCAL ANESTHETICS

[75] Inventors: Julius Diamond, Morris Plains, N.J.; George H. Douglas, Malvern, Pa.

[73] Assignee: William H. Rorer, Inc., Fort Washington, Pa.

[21] Appl. No.: 800,496

[22] Filed: May 25, 1977

Related U.S. Application Data

[60] Division of Ser. No. 671,762, Mar. 30, 1976, abandoned, which is a continuation-in-part of Ser. No. 558,187, Mar. 31, 1975, Pat. No. 4,060,635.

[51] Int. Cl.² ............................................ A61K 31/17
[52] U.S. Cl. ..................... 424/322; 424/244; 424/246; 424/248.54; 424/250; 424/267; 424/270; 424/274
[58] Field of Search ........................................ 424/322

[56] References Cited

U.S. PATENT DOCUMENTS 3,761,597   9/1973   Walls ................................... 424/304

Primary Examiner—Frederick E. Waddell
Attorney, Agent, or Firm—James A. Nicholson; John C. Smith, Jr.

[57] ABSTRACT

A method for producing local anesthetic action in a patient by administering amidinoureas.

10 Claims, No Drawings

AMIDINOUREA LOCAL ANESTHETICS

CROSS REFERENCE TO RELATED APPLICATIONS

This is a division of our co-pending application Ser. No. 671,762 filed Mar. 30, 1976, now abandoned, which is a continuation-in-part of our co-pending application Ser. No. 558,187 filed Mar. 31, 1975, now U.S. Pat. No. 4,060,635 issued Nov. 29, 1977.

SUMMARY OF THE INVENTION

This invention describes a new class of chemical compounds and the process for their preparation. This invention also describes a new method for producing local anesthetic and anti-arrhythmic actions. This invention further provides valuable pharmaceutical preparations which are effective for producing local anesthetic and anti-arrhythmic actions. This invention further describes a class of chemical compounds called amidinoureas and the same possess an effective degree of activity which is capable of producing local anesthetic and anti-arrhythmic properties in mammals.

BACKGROUND OF THE INVENTION

Local anesthetics block nerve conduction when applied locally to nerve tissue. They may act on any part of the nervous sytem and on every type of nerve fiber or they may act selectively between different types of nervous tissue such as central nervous tissue or peripheral nervous tissue or myelinated or non-myelinated fibers. The advantage with useful local anesthetics is that their action is reversible and nerve function is restored with no evidence of structural damage to nerve fibers or cells. Continued studies have been carried out in research to develop drugs which would have all the desirable properties of a good local anesthetic agent. Such properties would necessarily be non-irritating to the tissue with which it is in contact or cause any permanent damage to nerve structure. Further, its sustemic toxicity should be low. The ideal local anesthetic should be effective regardless whether it is injected into the tissue or applied locally to mucous membranes. The time for onset should also be as short as possible while its action should last long enough for the need indicated, and the recovery period should be one which is of a suitable duration.

Anti-arrhythmic agents have been long sought by the researchers. The principal anti-arrhythmic drugs of long established usefulness are quinidine and procainamide. More recently lidocaine, phenytoin and propranolol have been found to be helpful in establishing certain anti-arrhythmic disorders. Each of these agents, however, has been found to have certain drawbacks and great care must be used when they are employed for the treatment of arrhythmic disorders. The ideal antiarrhythmic agent would be one having a minimal amount of side effects while at the same time being orally active, typical side effect being myocardial depression and CNS deficit. The most serious form of arrhythmia is fibrillation and a high degree of protection against this particular disorder would be most beneficial.

We have unexpectedly found potent anti-arrhythmic and local anesthetic agents.

We have unexpectedly found a class of chemical compounds which have anti-arrhythmic and local anesthetic properties without accompanying side effects which are common with these agents.

We have further found unexpectedly that amidinourea compounds are effective anti-arrhythmic agents which act orally.

We have also unexpectedly found a means of providing protection against fibrillation.

We have also unexpectedly found that administration of amidinoureas is a simple and effective method for the treatment of anti-arrhythmic disorders.

We have still further found effective local anesthetic agents which are non-irritating to the tissue, do not cause permanent damage to their structure, their sustemic toxicity is low, and they are effective when applied by injection into the tissue or applied locally. These agents have also been found to have a desirable onset period while their action may be extended for periods of time depending on the use intended.

DESCRIPTION AND PREFERRED EMBODIMENTS

This invention describes a novel class of chemical compounds of the formula

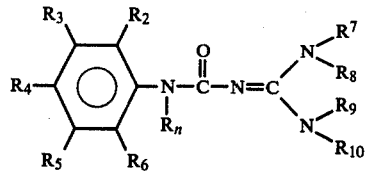

where:

$R_2$, $R_3$, $R_4$, $R_5$ and $R_6$ may be the same or different and are; hydrogen,
halo,
loweralkyl,
haloloweralkyl,
nitro,
amino, acylamino,
hydroxy,
aralkyloxy or
loweralkoxy;

$R_7$, $R_8$, $R_9$ and $R_{10}$ may be the same or different and are:
hydrogen,
alkyl,
alkenyl,
alkynyl,
cycloalkyl,
cycloalkenyl,
cycloalkylloweralkyl,
alkoxyloweralkyl,
aralkoxyloweralkyl or
aralkyl;

$R_7$ and $R_8$ together and $R_9$ and $R_{10}$ together may form a 5–7 atom ring which may further include 0–1 hetero atoms of N, O or S;

$R_n$ is hydrogen or loweralkyl provided at least one of $R_7$, $R_8$, $R_9$ and $R_{10}$ is other than hydrogen; and
the non-toxic acid addition salts thereof.

In any discussion of the true structure of an amidinourea, tautomerism must be considered. It should be clear to anyone skilled in the art that the amidinourea sidechain can be legitimately represented in any one of several tautomeric and geometric modifications.

The total number of possible variations in structure is quite high, but it is true to say that these variations can and, to some extent, do occur when these compounds are in solution.

One form may predominate over another depending upon the degree and location of substitution and on the nature of the solvent. The rates of conversion of one tautomer to another will depend upon the nature of the solvent, the degree of hydrogen bonding permitted, the temperature and possibly other factors (such as pH, trace impurities and the like).

To illustrate what is meant by this, a number of likely structures are here shown for just one of the compounds in this invention.

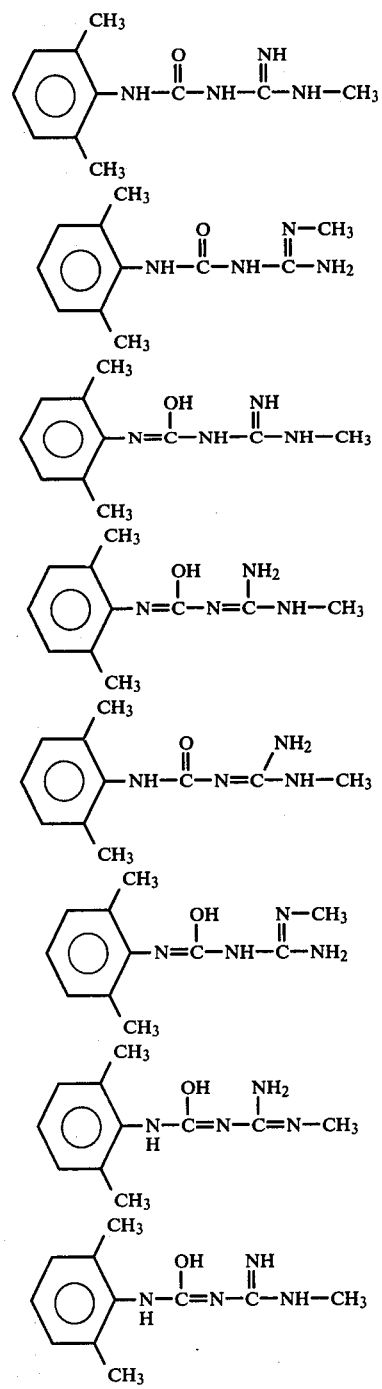

Of course, other types of structures are possible such as those with hydrogen bonding.

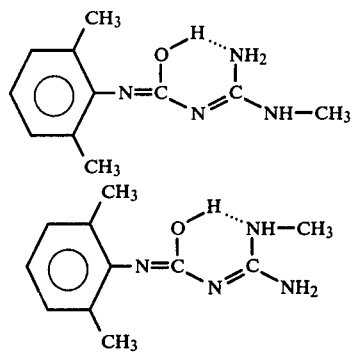

No attempt is made to exhaust the possible structures, for these are legion. The structures given are representative of the kind of phenomenon we are trying to describe and are encompassed within the scope of this invention.

It is predictable that in physiological conditions, any or all of these structures may exist or even predominate at the sites at which these molecules operate.

Tautomerism, of course, by definition only applies to protons and not to other groups. Thus, in the example given, free conversion between structures occurs smoothly by transference of a single proton. At a time where other substituents are concerned, tautomerism is to just that extent ruled out. For example where there are no protons at all because of full substitution, only one structure may be reasonably said to exist such as:

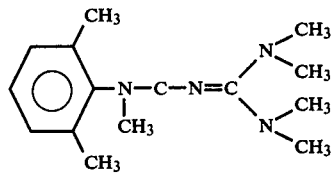

Compounds of this invention which are preferred include those where:
$R_2$, $R_3$, $R_4$, $R_5$ and $R_6$ are hydrogen,
  halo,
  loweralkyl,
  haloloweralkyl,
  nitro or
  loweralkoxy; and
$R_7$, $R_9$ and $R_n$ are hydrogen or loweralkyl;
$R_8$ and $R_{10}$ are hydrogen or alkyl, alkenyl, alkynyl, alkoxyloweralkyl and aralkoxyalkyl provided $R_7$, $R_8$, $R_9$ and $R_{10}$ are not all hydrogen at the same time; and
$R_7$ and $R_8$ together and $R_9$ and $R_{10}$ together are alkylidenyl.

The more preferred compounds of this invention include those where:
$R_2$ is hydrogen or loweralkyl;
$R_3$ and $R_5$ are hydrogen;
$R_4$ is hydrogen,
  loweralkyl or halo
$R_6$ is hydrogen,
  loweralkyl, nitro,
  alkoxy or halo;
$R_7$, $R_9$ and $R_n$ are hydrogen or loweralkyl; and
$R_8$ and $R_{10}$ are hydrogen or alkyl,
  alkenyl,
  alkynyl, alkoxyloweralkyl or
aralkoxyloweralkyl; provided R7, R8, R9 and R10 are not all hydrogen at the same time;

R7 and R8 together and R9 and R10 together are alkylidenyl.

The most preferred compounds of this invention are those where;

R2 is hydrogen, methyl or ethyl;
R3 and R5 are hydrogen;
R4 is hydrogen, mthyl, ethyl, chloro or bromo;
R6 is hydrogen,
   methyl, ethyl
   nitro,
   methoxy,
   ethoxy,
   chloro
   bromo or
   fluoro;
Rn is hydrogen,
   methyl or ethyl, and
R7, R8, R9 and R10 are hydrogen,
   methyl,
   ethyl,
   propyl,
   i-propyl,
   butyl,
   i-butyl,
   sec-butyl,
   t-butyl,
   pentyl,
   hexyl,
   heptyl,
   allyl,
   propargyl,
   methoxyethyl
   ethoxyethyl
   benzyloxyethyl; provided R7, R8, R9 and R10 are not all hydrogen at the same time; and
R7 and R8 together and R9 and R10 together are tetramethylene, pentamethylene and hexamethylene.

A special embodiment of this invention comprises compounds which have:
R2-loweralkyl substitution;
R2, R6-diloweralkyl substitution;
R2, R6-loweralkyl, alkoxy substitution;
R2, R6-loweralkyl, halo substitution;
R2, R6-alkyl, nitro substitution;
R2, R4, R6-triloweralkyl substitution, or
R2, R4, R6-loweralkyl, dihalo substitution.

A further special embodiment of this invention comprises compounds which have:
R2, R6-dihalo substitution.

A further special embodiment of this invention comprises compounds which have:
R7, R8, R9 and R10 are hydrogen or loweralkyl substitution all are not hydrogen at the same time;
R7, R8 and R9 are hydrogen or loweralkyl and R10 is an alkyl, alkenyl or alkynyl group from 3 to 7 carbon atoms; or
R7, R8 and R9 are hydrogen or loweralkyl and R10 is an aralkoxyloweralkyl group.

This invention further describes a novel method for producing local anesthetic and anti-arrhythmic properties by the administration of a compound of the formulae:

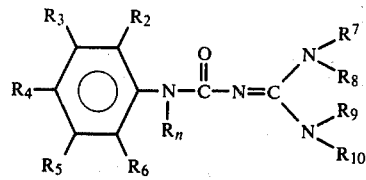

where:
R2, R3, R4, R5 and R6 may be the same or different and are:
   hydrogen,
   halo,
   loweralkyl,
   haloloweralkyl,
   nitro
   amino, acylamino or
   loweralkoxy and
Rn is hydrogen or
   loweralkyl;
R7, R8, R9 and R10 are:
   hydrogen,
   alkyl,
   alkenyl,
   alkynyl,
   cycloalkyl,
   cycloalkenyl,
   cycloalkylloweralkyl,
   alkoxyloweralkyl
   aralkoxyloweralkyl or
   aralkyl;
R7 and R8 together and R9 and R10 together may form a 5-7 atom ring which may further include 0-1 hetero atoms of N, O or S; and
the non-toxic acid addition salts thereof.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:

| | |
|---|---|
| hydrochloric acid, | succinic acid, |
| hydrobromic acid, | glycolic acid, |
| sulfuric acid, | lactic acid, |
| nitric acid, | salicylic acid, |
| phosphoric acid, | benzoic acid, |
| methane sulfonic acid, | nicotinic acid, |
| benzene sulfonic acid, | phthalic acid, |
| acetic acid, | stearic acid, |
| propionic acid, | oleic acid, |
| malic acid, | abietic acid, etc. |

The nomenclature applied to the compounds of this invention is based on the urea moiety as follows:

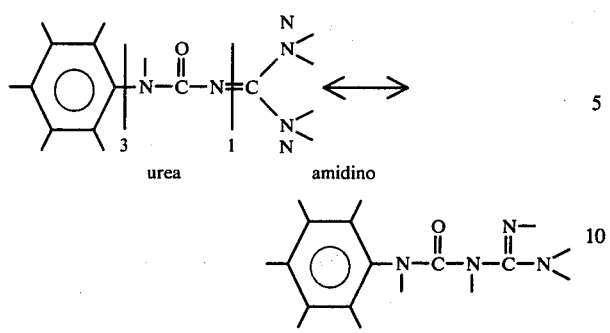

The term "loweralkyl" refers to an alkyl hydrocarbon group from 1 to 5 carbon atoms which may be straight chained or branched while "alkyl" refers to an alkyl hydrocarbon group which may have as many as ten carbon atoms.

The term "alkenyl" refers to an alkenyl hydrocarbon chain having 3–7 carbon atoms.

The term "alkynyl" refers to an alkynyl hydrocarbon chain having 3–7 carbon atoms.

The term "cycloalkyl" refers to a cycloalkyl group having 3–7 carbon atoms.

The term "cycloalkenyl" refers to a cycloalkenyl group having 5–7 carbon atoms.

The "loweralkoxy" radical signifies an alkoxy group containing from 1 to about 5 carbon atoms which may be straight chained or branched.

The preferred "aryl" group is phenyl.

The preferred "aralkyl" groups are benzyl and phenethyl.

The preferred "haloloweralkyl" group is trifluoromethyl.

The preferred "haloloweralkoxy" group is trifluoromethoxy.

The compounds of this invention may be prepared by the following general synthesis:

It is convenient to generate the substitute guanidine in situ by hydrolyzing a salt of the guanidine with base in the reaction medium. The appropriate isocyanate is then added dropwise into the well-stirred reaction mixture. Condensation of a substitutedphenyl isocyanate (prepared from an aniline and phosgene in the customary manner) with guanidine results in a 1-substitutedphenyl-3-amidinourea. The reaction is carried out in a polar medium using solvents such as dimethylformamide, tetrahydrofuran, etc.

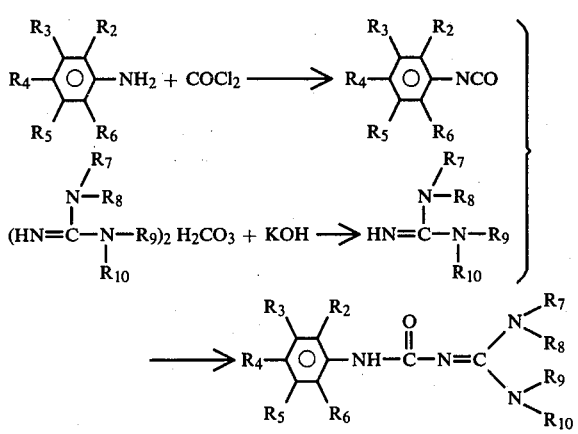

These compounds may also be prepared by degradation of the corresponding biguanide. When a 1-substitutedphenylbiguanide compound is hydrolyzed in acid at raised temperature then the resultant product is 1-substitutedphenyl-3-amidinourea. This reaction is preferably carried out using hydrochloric acid and the reaction time and reaction temperature will of course depend on the particular biguanide used and the concentration of the acid present. In general, the more concentrated acids will not require high temperatures or long periods of reaction time.

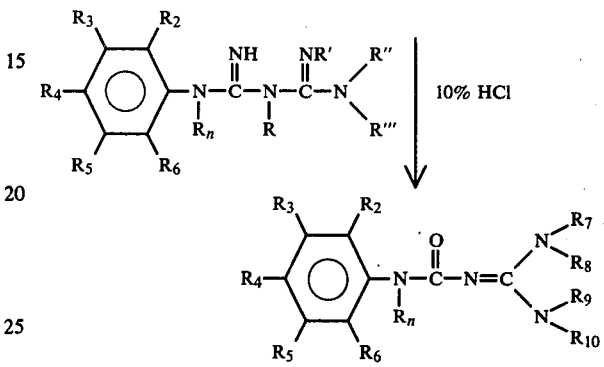

When it is desired to have $R_n$ substitution at the N-3 the starting material of course will be an aniline having N-alkyl substitution. Reaction with phosgene results in the carbamoyl chloride which is then reacted with the substituted guanidines to prepare the amidinourea.

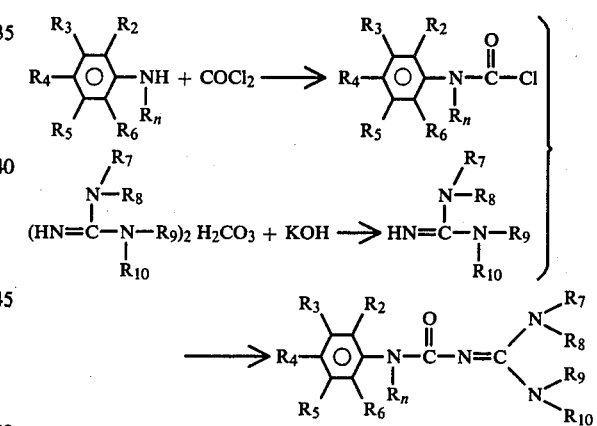

The starting anilines are either known, may be prepared by known techniques or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (Cl I).

Alkylation may be carried out on an acetanilide using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound.

Diazotization followed by a Sandmeyer type reaction may yield the bromo, chloro or iodo compound.

A chloro, bromo or iodo compound may also be reacted with trifluoromethyliodide and copper powder at about 150° C. in dimethylformamide to obtain a trifluoromethyl compound [Tetrahedron Letters: 47, 4095 (1959)].

Reactions may also be carried out at other stages of synthesis depending on the substituents present and the substituents desired and various combinations of the foregoing reactions will be determined by one skilled in the art in order that the desired product results. Thus, a phenylamidinourea may be halogenated or nitrated as above, etc.

The biguanide starting materials are also either known, may be prepared by known procedures or may be prepared by the following general synthesis:

Condensation of cyanoguanidine and an aniline in the presence of an equimolar amount of a mineral acid results in the corresponding phenylbiguanide:

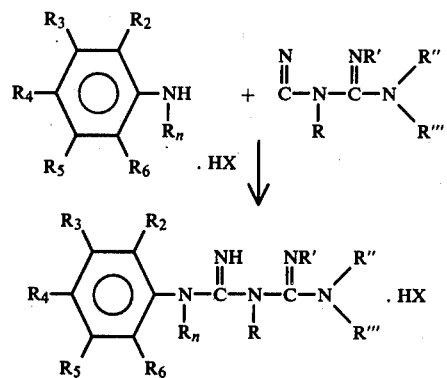

This reaction is preferably carried out on the aniline salt either in a polar medium or neat and using increased temperatures. The appropriately substituted product may be prepared by the reactions above when the same are also carried out in the biguanide or amidinourea.

We have found that the compounds of this invention exercise a useful degree of local anesthetic and anti-arrhythmic activity in mammals; as such they are effective in producing local anesthetic actions and in the treatment or conversion of known arrhythmias or for the protection against fibrillation. In general, the compounds of this invention are indicated for a wide variety of mammalian conditions where the use of a local anesthetic is necessary. These compounds when used as an anti-arrhythmic agent are found to be effective against arrhythmias of atrial and ventricular origin. For these purposes, the compounds of this invention are normally administered parenterally and/or topically as local anesthetic agents and they may also be administered orally or parenterally for anti-arrhythmic indications.

Orally, they may be administered in tablets, aqueous or oily suspensions, dispersible powders or granules, emulsions, hard or soft capsules, or syrups or elixirs. The term "parenteral" as used herein includes subcutaneous, intravenous, intramuscular or intrasternal injections or infusion techniques.

Compositions intended for oral use may be prepared according to any method known to the art for the manufacture of pharmaceutical compositions and such compositions may contain one or more agents selected from the group consisting of sweetening agents, flavoring agents, coloring agents and preserving agents, in order to provide a pharmaceutically elegant and palatable preparation. Tablets which contain the active amidinourea ingredient in admixture with non-toxic pharmaceutically acceptable excipients are suitable for the manufacture of tablets. These excipients may be, for example, inert diluents, for example, calcium carbonate, sodium carbonate, lactose, calcium phosphate or sodium phosphate; granulating and disintegrating agents, for example, maize starch or alginic acid; binding agents, for example, starch, gelatin or acacia; and lubricating agents, for example, magnesium stearate, stearic acid or talc. The tablets may be uncoated or they may be coated by known techniques to delay disintegration and absorption.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active amidinourea form a further embodiment of this invention. Excipients suitable for aqueous suspensions, may be employed if desired. These excipients are suspending agents, for example, sodium carboxymethyl-cellulose, methyl-cellulose, hydroxypropylmethylcellulose, sodium alginate, polyvinylpyrrolidine, gum tragacanth and gum acacia; dispersing or wetting agents may be a naturally occurring phosphatide, for example, lecithin; or condensation products of an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol mono-oleate; or condensation products of ethylene oxide with partial esters derived from fatty acids and hexitol anhydrides, for example, polyoxyethylene sorbitan monooleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate. The emulsions may also contain sweeping and flavoring agents.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, for example, as an aqueous solution buffered to a pH of 4.0 to 7.0 and made isotonic with sodium chloride.

Further, the active amidinourea may be administered alone or in admixture with other agents having the same or different pharmacological properties.

Further, these compounds may be tableted or otherwise formulated for oral use so that for every 100 parts by weight of the composition, there are present between 5 and 95 parts by weight of the active ingredient. The dosage unit form will generally contain between about 1 mg. and about 500 mg. of the active ingredients of this invention. The preferred unit dose is between about 10 mg. and about 100 mg. The compositions may be taken 1–8 times daily depending on the dosage unit required.

The dosage regimen in carrying out the methods of this invention is that which insures maximum therapeutic response until improvement is obtained and thereafter the minimum effective level which gives relief. Thus, in general, the dosages are those that are therapeutically effective in the treatment of arrhythmias and producing local anesthetic actions. In general, the oral daily dose can be between about 0.1 mg/kg and 70 mg/kg (preferably in the range of 0.5–50 mg/kg/day), bearing in mind, of course, that in selecting the appropriate dosage in any specific case, consideration must be given to the patient's weight, general health, age, and other factors which may influence response to the drug.

Parenteral administration may be carried out using comparative dosages taken from the oral compositions. In general, the parenteral dosage will be less than the oral dose and normally within the range of ½ to 1/10 the oral dose but, of course, this would depend on the absorption characteristics of the compound employed. Dosages would be in the customary manner; however, in general, parenteral administration may be carried out neat or the compound may be utilized with a sterile vehicle as mentioned above. Dosage unit forms between 1 mg. and 500 mg. and preferably in the range of 10 mg. and 100 mg. are useful. The daily parenteral dose would be between 0.1 mg/Kg/day and 70 mg/Kg/day and preferably in the range of 0.5 mg/Kg and 50 mg/Kg/day.

These compounds may further be formulated for topical administration in the usual manner. Preferred formulations in the form of a gel or paste or the like may contain the active ingredient in the range of 0.1–10% by weight of the composition.

Various tests can be carried out in animal models to show the ability of the amidinoureas of this invention to exhibit reactions that can be correlated to anti-arrhythmic properties and local anesthetic activity in humans. The following tests show the ability of the compounds of this invention to produce local anesthetic actions in animals and are known to correlate well with local anesthetic activity in humans. These are considered to be standard tests used to determine local anesthetic properties. This correlation can be shown by the activities of compounds known to be clinically active. In view of the results of these tests, the amidinoureas of this invention can be considered to be local anesthetic agents.

The following tests are used in order to determine the effectiveness of the amidinoureas of this invention and their anti-arrhythmic properties.

Harris Dog Induced Arrhythmia

In 1950, Harris published a technique for induction of acute myocardial infarction in dogs which has become accepted as a useful method for studying the efficacy of anti-arrhythmic agents. Generally, ventricular arrythmias arise 4 to 8 hours after acute myocardial infarction and persist for 48 to 72 hours. It is felt that the arrythmias originate in subendocardial Purkinje cells within or near the site of the infarction and are due to enhanced automaticity within these cells. We have employed this model for the evaluation of oral anti-arrythmic efficacy of the amidinoureas of this invention.

Methods

Healthy male mongrel dogs 9.5–15 kg. were anesthetized with intravenous sodium pentobarbital (30 mg/kg) and the trachea was intubated and respired with room airwith a Harvard respirator. Under aseptic conditions, the chest was opened through a small left thoracotomy at the fourth or fifth intercostal space and the pericardium incised near the left atrial appendage. The left anterior descending coronary artery was isolated approximately 5–10 mm distal to the left atrial appendage without traumatizing the associated coronary vein. A double ligature was passed under the coronary artery. One of the ligatures was firmly tied around a 20 g. needle barrel overlying the coronary artery, and the needle immediately extracted. This procedure results in a 20–50% constriction of the coronary artery at the site of the ligature. After 20 minutes, the second ligature was tied in order to completely occlude the distal portion of the left anterior coronary artery. The lungs were then expanded. The chest wall was closed and the thoracic cavity evacuated. The dogs were allowed to recover from anesthesia with supplementary morphine or Tranvet (propiopromazene HCl) administered as needed to prevent unnecessary pain. Antibiotics were given prophylactically.

Eighteen to 24 hours after surgery, the dogs were placed in cages in a quiet environment with water constantly available. At this time the dogs were able to walk freely around the cage and showed no signs of obvious discomfort. The Lead II electrocardiogram was monitored continuously and recorded on a Beckman Dynograph recording system. Recordings were made on a scheduled basis before and after administration of gelatin capsules containing the amidinourea (10 mg/kg) or placebo. Normal and abnormal beats were counted and expressed as a ratio of normal beats/total beats per unit time. Only beats of sinoatrial origin were considered normal.

The dogs were generally given the first capsule after recording the EKG for 40-60 minutes. After three hours a second capsule was given and EKGs were monitored for an additional three hours. The dogs were then fed. Forty-eight hours after surgery, the dogs were again monitored according to the schedule employed on the first day.

At the end of the second day, the dogs were sacrificed with an intravenous overdose of sodium pentobarbital. Hearts were extracted and examined to determine the size and area of the induced infarct.

In view of these tests it is concluded that oral administration of amidinoureas of this invention produce a significant reduction in the incidence of ventricular ectopic rhythm in dogs with myocardial infarctions.

Chloroform-Induced Fibrillation in the Mouse

A slightly modified version of the procedure described by Lawson (J. Pharm. Exp. Ther. 160:22-31, 1968) is used.

Methods

Groups of five female Swiss Webster mice, 18 to 23 gm. were given i.p. injections of saline (0.1 ml/10 gm body wt.) or the amidinourea (at equivalent volumes). The amidinourea was administered at doses of 50, 25, 12.5, 6.25 and 3.125 mg/kg body wt. Saline was administered to two control groups. After 10 minutes, each mouse was placed in a 1000 ml. beaker containing a gauze pad saturated with 20-30 ml. of chloroform. Each mouse was removed from the beaker immediately after respiratory arrest and the thoracic cavity opened for visual determination of ventricular activity. Each mouse was scored for the presence of ventricular rhythm or ventricular fibrillation for 15-20 sec. If ventricular fibrillation was observed, the heart was stroked lightly with a forceps in an effort to induce ventricular rhythm. Maintenance of at least five consecutive ventricular beats following cardiac stroking was scored as ventricular rhythm despite the initial observation of fibrillation.

The results of these studies indicate that the amidinourea of this invention are useful in maintaining sustained ventricular rhythm despite the presence of conditions for ventricular fibrillation.

Other tests used to determine the effectiveness of the compounds of this invention as anti-arrhythmic agents included:

Ventricular arrhythmias after coronary artery ligation. One-step ligation. Fifteen mongrel dogs of either sex, weight 11 to 15 kg. were anesthetized with pentobarbital sodium, 30 mg/kg i.v. A tracheostomy was performed and the animals were ventilated under positive pressure at a minute volume determined from a body weight nomogram. Blood pressure was measured from the femoral artery via a Statham pressure transducer. A thoracotomy was performed in the left 4th intercostal space and the heart was exposed. The left atrial appendage was reflected and a ligature was passed under the left anterior descending coronary artery near its origin distal to the first major septal perforator. The free ends of the ligature were passed through a short section of polyethylene tubing. The artery could then be occluded by pressing the tubing onto the vessel while pulling up on the free ends of the ligature. The occlusion was maintained for 20 minutes by clamping the ligature with Kelly forceps. If the animal survived, the occlusion was released and blood flow restored by releasing the clamp and pulling the tubing away from the vessel. The lead II electrocardiogram was monitored continuously on an oscilloscope and continuous recordings were made on a Beckman oscillograph.

Anesthetized, Ouabain-Intoxicated Dog

Ventricular tachycardia and/or multifocal ventricular ectopic rhythms induced by intoxication with ouabain in anesthetized dogs have been used as a classical method for evaluation of anti-arrhythmic activity. We have employed this procedure for initial evaluation of anti-arrhythmic activity of compounds in the amidinourea series, and in recent studies have attempted to determine their relative effectiveness using several modifications of the basic method.

Methods

Male mongrel dogs weighing 8-12 kg. were anesthetized with pentobarbital sodium, 30 mg/kg i.v. Arterial blood pressure was measured with a Statham transducer and a Beckman Dynagraph recording system via a femoral arterial catheter. The femoral vein was cannulated for administration of ouabain or the test compounds. Standard Lead II electrocardiograms were monitored and used to drive a Beckman Cardiotachometer.

Ouabain (Strophanthin G, obtained from Schwarz/Mann) was initially administered at 40 $\mu$gm/kg i.v. with additional injections of 10 $\mu$gm/kg i.v. at 15 minute intervals until sustained ventricular tachycardia or multifocal ventricular ectopic beats were observed. Such arrhythmias are generally maintained, but in our studies anti-arrhythmic activity was monitored for a maximum of 60 minutes, since spontaneous conversions to normal sinus rhythm may occur after this period of time.

Three different procedures have been used to determine the effective local anesthetic properties of the compounds of this invention. These tests have been used extensively in the past and have been proven to provide satisfactory results in establishing local anesthetic properties of compounds and provide sufficient results to enable one to use the same.

A discussion of these experimental methods which would enable the skilled artisan to carry out this invention in the manner he sees fit will be found in *Evaluation of Drug Activities: Pharmacometrics*, Vol. 1, Ed by D. R. Lawrence and A. L. Bacharach, Academic Press, Inc. (London) Ltd. (1964). Applicants herewith incorporate by reference Chapter 9 of this book entitled, "Local Anesthetics", pages 205-214.

The following are detailed examples which show the properties of the compounds of this invention. They are to be construed as illustrations of said compounds and not as limitations thereof.

EXAMPLE 1

1-(2',6'-Dimethylphenyl)-3-methylamidinourea hydrochloride

A. 2,6-Dimethylaniline [250 g. (2.06 moles)] is dissolved in 2.5 l. of toluene at room temperature. The mixture is stirred mechanically while liquid phosgene

[300 ml. (4.2 moles)] is distilled in through a tube introduced below the surface of the toluene. When addition of the phosgene is complete, the mixture is heated to reflux for two hours after which time, the reaction is essentially complete.

The first 500 ml. of distillate (containing most of the phosgene excess) is now allowed to distil over, and the remainder of the toluene is removed by vacuum distillation.

The residual crude isocyanate is distilled under vacuo to give 2,6-dimethylphenylisocyanate as a clear colorless liquid having a b.p. 58° at 1 mm.

B. Methylguanidine sulfate [665 g. (2.72 moles)] sodium hydroxide solution (50% w/w, 435 g.) and tetrahydrofuran (1250 ml.) are combined with vigorous stirring for 2 hours, after which time, with continued stirring, a solution of 2,6-dimethylphenylisocyanate [400 g. (2.72 moles = 2 equivalents)] in tetrahydrofuran 1 l. is added dropwise.

After addition is complete, (7 hours) the mixture is stirred overnight (14 hours) then concentrated to dryness in vacuo. The residue is diluted with water (3500 ml.) and basified to pH 12 with concentrated sodium hydroxide solution. (200 ml.). Ether (300 ml.) is added and after 45 minutes the white solid thus obtained is filtered and washed thoroughly with water, then with ether (1 l.) Enough methanol is added to dissolve the precipitate (approximately 4 l.). The methanol solution is dried with anhydrous sodium sulfate then filtered.

The clear filtered solution is acidified to pH 4 or less by addition of methanol saturated with hydrogen chloride, then the mixture is evaporated to dryness. The residual solid is ground and triturated with ether, filtered, and washed with ether. The product is dried in vacuo at 80° C. for 2 hours to give 1-(2',6'-dimethylphenyl)-3-methylamidinourea hydrochloride (m.p. 194°–197°).

EXAMPLE 2

When methylguanidine sulfate in Example 1 is replaced by the guanidines sulfate of the compounds of Table I below, then the corresponding product of Table II below is prepared.

TABLE I ethylguanidine sulfate
propylguanidine sulfate
i-propylguanidine sulfate
butylguanidine sulfate
i-butylguanidine sulfate
sec-butylguanidine sulfate
t-butylguanidine sulfate
pentylguanidine sulfate
hexylguanidine sulfate
heptylguanidine sulfate
octylguanidine sulfate
nonylguanidine sulfate
decylguanidine sulfate
allylguanidine sulfate
1-(3-butenyl)guanidine sulfate,
1-(2-pentenyl)guanidine sulfate
1-(4-hexenyl)guanidine sulfate
1-(5-heptenyl)guanidine sulfate
propargylguanidine sulfate
1-(2-butynyl)guanidine sulfate
1-(3-heptynyl)guanidine sulfate
cyclopropylguanidine sulfate
cyclobutylguanidine sulfate
cyclopentylguanidine sulfate
cyclohexylguanidine sulfate
cycloheptylguanidine sulfate
1-(2-cyclopentenyl)guanidine sulfate
1-(3-cyclopentenyl)guanidine sulfate
1-(2-cyclohexenyl)guanidine sulfate
1-(3-cyclohexenyl)guanidine sulfate
1-(2-cycloheptenyl)guanidine sulfate
1-(3-cycloheptenyl)guanidine sulfate
1-(4-cycloheptenyl)guanidine sulfate
cyclopropylmethylguanidine sulfate
cyclopropylethylguanidine sulfate
cyclobutylmethylguanidine sulfate
cyclobutylethylguanidine sulfate
cyclopentylethylguanidine sulfate
cyclohexylpropylguanidine sulfate
benzyloxyethylguanidine sulfate
phenethoxyethylguanidine sulfate
benzyloxypropylguanidine sulfate
phenethoxypropylguanidine sulfate
methoxyethylguanidine sulfate
ethoxyethylguanidine sulfate
benzylguanidine sulfate
phenethylguanidine sulfate
1,1-dimethylguanidine sulfate
1,2-dimethylguanidine sulfate
1,1,2-trimethylguanidine sulfate
1,1,-diethylguanidine sulfate
1,2-diethylguanidine sulfate
1,1,2-triethylguanidine sulfate
1-ethyl-1-methylguanidine sulfate
1-ethyl-2-methylguanidine sulfate
1,1-dimethyl-2-ethylguanidine sulfate
1,1-diethyl-2-methylguanidine sulfate
1-methyl-1-propylguanidine sulfate
1-methyl-2-propylguanidine sulfate
1-methyl-1-butylguanidine sulfate
1-methyl-2-butylguanidine sulfate
1,1-dimethyl-2-propylguanidine sulfate
1,1-dimethyl-1-butylguanidine sulfate
1,1-dipropylguanidine sulfate
1,2-dipropylguanidine sulfate
1-ethyl-1-propylguanidine sulfate
1-ethyl-2-propylguanidine sulfate
1-methyl-2-pentylguanidine sulfate
1-methyl-2-hexylguanidine sulfate
1-methyl-2-heptylguanidine sulfate
1-methyl-2-allylguanidine sulfate
1-methyl-2-propargylguanidine sulfate
1-methyl-2-cyclopropylguanidine sulfate
1-methyl-2-(2'-cyclopentenyl)guanidine sulfate
1-methyl-2-cyclopropylmethylguanidine sulfate
1-methyl-2-benzyloxyethylguanidine sulfate
1-methyl-2-phenethoxyethylguanidine sulfate
1-methyl-2-benzyloxypropylguanidine sulfate
1-methyl-2-phenethoxypropylguanidine sulfate
1-methyl-1-benzyloxypropylguanidine sulfate
1-methyl-1-phenethoxyethylguanidine sulfate 1-methyl-1-benzyloxyethylguanidine sulfate
1,2-dimethyl-2-benzyloxyethylguanidine sulfate
1-methyl-2-benzylguanidine sulfate
1-methyl-2-phenethylguanidine sulfate
1-ethyl-2-benzyloxyethylguanidine sulfate
1-propyl-2-benzyloxyethylguanidine sulfate
1,1-tetramethyleneguanidine sulfate
1,1-pentamethyleneguanidine sulfate
1,1-hexamethyleneguanidine sulfate
1,1-(3'-oxapentamethylene)guanidine sulfate 1,1-(N-methyl-3'-azapentamethylene)guanidine sulfate
1,1-(N-methyl-3'-azahexamethylene)guanidine sulfate
1,1,2,2-tetramethylguanidine sulfate
1,1-dimethyl-2,2-diethylguanidine sulfate
1,2-dimethyl-1,2-diethylguanidine sulfate
1,1,2-trimethyl-2-ethylguanidine sulfate
1,1,2,2-tetraethylguanidine sulfate
1,1,2,2-tetrapropylguanidine sulfate
1,1,2,2-tetrabutylguanidine sulfate
1-methyl-2-ethyl-1,2-dipropylguanidine sulfate
1,1-pentamethylene-2-methylguanidine sulfate
1,1-pentamethylene-2,2-pentamethyleneguanidine sulfate
1,1-tetramethylene-2-methylguanidine sulfate
1,1-pentamethylene-2,2-dimethylguanidine sulfate
1,1-pentamethylene-2,2-tetramethyleneguanidine sulfate
1,1-pentamethylene-2-methyl-2-ethylguanidine sulfate
1,1-tetramethylene-2-allylguanidine sulfate
1,1-tetramethylene-2-benzyloxyethylguanidine sulfate
1,1-tetramethylene-2-propargylguanidine sulfate
1-methyl-1-propargyl-2-ethyl-2-pentylguanidine sulfate
1,1-hexamethylene-2-methylguanidine sulfate
1,1-hexamethylene-2,2-dimethylguanidine sulfate
1,1-(3'-oxapentamethylene)-2-methylguanidine sulfate
1,1-(N-methyl-3'-azahexamethylene)-2,2-dimethylguanidine sulfate
1,1-(N-methyl-3'-azahexamethylene)-2,2-tetramethyleneguanidine sulfate
1-(3'-butynyl)guanidine sulfate
1-(2-butenyl)guanidine sulfate
1-methyl-1-allylguanidine sulfate
1-methyl-1-propargylguanidine sulfate
1-methyl-1-cyclopropylmethylguanidine sulfate
1-methyl-1-methoxyethylguanidine sulfate
1-methyl-1-benzyloxyethylguanidine sulfate
1,1-tetramethylene-2-ethylguanidine sulfate
1,1-tetramethylene-2,2-tetramethylene
1,1-(2'-thiapentamethylene)guanidine sulfate
1,1-(2'-thiatetramethylene)guanidine sulfate

TABLE II 1-(2',6'-dimethylphenyl)-3-ethylamidinourea hydrochloride
1-(2',6'-dimethylphenyl)-3-propylamidinourea hydrochloride
1-(2',6'-dimethylphenyl)-3-i-propylamidinourea hydrochloride
1-(2',6'-dimethylphenyl)-3-butylamidinourea hydrochloride
1-(2',6'-dimethylphenyl)-3-i-butylamidinourea hydrochloride
1-(2',6'-dimethylphenyl)-3-sec-butylamidinourea hydrochloride
1-(2',6'-dimethylphenyl)-3-t-butylamidinourea hydrochloride
1-(2',6'-dimethylphenyl)-3-pentylamidinourea hydrochloride
1-(2',5'-dimethylphenyl)-3-hexylamidinourea hydrochloride
1-(2',6'-dimethylphenyl)-3-heptylamidinourea hydrochloride
1-(2',6'-dimethylphenyl)-3-octylamidinourea hydrochloride
1-(2',6'-dimethylphenyl)-3-nonylamidinourea hydrochloride
1-(2',6'-dimethylphenyl)-3-decylamidinourea hydrochloride
1-(2',6'-dimethylphenyl)-3-allylamidinourea hydrochloride
1-(2',6'-dimethylphenyl)-3-[N-(3'-butenyl)amidino]urea hydrochloride
1-(2',6'-dimethylphenyl)-3-[N-(2'-pentenyl)amidino]urea hydrochloride
1-(2',6'-dimethylphenyl)-3-[N-(4'-hexenyl)amidino]urea hydrochloride
1-(2',6'-dimethylphenyl)-3-[N-(5'-heptenyl)amidino]urea hydrochloride
1-(2',6'-dimethylphenyl)-3-propargylamidinourea hydrochloride
1-(2',6'-dimethylphenyl)-3-(N-allyl-N-methylamidino)urea hydrochloride
1-(2',6'-dimethylphenyl)-3-[N-(3'-heptynyl)amidino]urea hydrochloride
1-(2',6'-dimethylphenyl)-3-cyclopropylamidinourea hydrochloride
1-(2',6'-dimethylphenyl)-3-cyclobutylamidinourea hydrochloride
1-(2',6'-dimethylphenyl)-3-cyclopentylamidinourea hydrochloride
1-(2',6'-dimethylphenyl)-3-cyclohexylamidinourea hydrochloride
1-(2',6'-dimethylphenyl)-3-cycloheptylamidinourea hydrochloride
1-(2',6'-dimethylphenyl)-3-[N-(2'-cyclopentenyl)amidino]urea hydrochloride
1-(2',6'-dimethylphenyl)-3-[N-(3'-cyclopentenyl)amidino]urea hydrochloride 1-(2',6'-dimethylphenyl)-3-[N-(2'-cyclohexenyl)amidino]urea hydrochloride
1-(2',6'-dimethylphenyl)-3-[N-(3'-cyclohexenyl)amidino]urea hydrochloride
1-(2',6'-dimethylphenyl)-3-[N-(2'-cycloheptenyl)amidino]urea hydrochloride
1-(2',6'-dimethylphenyl)-3-[N-(3'-cycloheptenyl)amidino]urea hydrochloride
1-(2',6'-dimethylphenyl)-3-[N-(4'-cycloheptenyl)amidino]urea hydrochloride
1-(2',6'-dimethylphenyl)-3-cyclopropylmethylamidinourea hydrochloride
1-(2',6'-dimethylphenyl)-3-cyclopropylethylamidinourea hydrochloride
1-(2',6'-dimethylphenyl)-3-cyclobutylmethylamidinourea hydrochloride
1-(2',6'-dimethylphenyl)-3-cyclobutylethylamidinourea hydrochloride
1-(2',6'-dimethylphenyl)-3-cyclopentylethylamidinourea hydrochloride
1-(2',6'-dimethylphenyl)-3-cyclohexylpropylamidinourea hydrochloride
1-(2',6'-dimethylphenyl)-3-benzyloxyethylamidinourea hydrochloride
1-(2',6'-dimethylphenyl)-3-phenethoxyethylamidinourea hydrochloride
1-(2',6'-dimethylphenyl)-3-methoxyethylamidinourea hydrochloride
1-(2',6'-dimethylphenyl)-3-ethoxyetnylamidinourea hydrochloride
1-(2',6'-dimethylphenyl)-3-benzylamidinourea hydrochloride
1-(2',6'-dimethylphenyl)-3-phenethylamidinourea hydrochloride
1-(2',6'-dimethylphenyl)-3-(N,N-dimethylamidino)urea hydrochloride
1-(2',6'-dimethylphenyl)-3-(N,N'-dimethylamidino)urea hydrochloride 1-(2',6'-dimethylphenyl)-3-(N,N,N'-trimethylamidino)urea hydrochloride
1-(2',6'-dimethylphenyl)-3-(N,N-diethylamidino)urea hydrochloride
1-(2',6'-dimethylphenyl)-3-(N,N'-diethylamidino)urea hydrochloride
1-(2',6'-dimethylphenyl)-3-(N,N,N'-triethylamidino)urea hydrochloride
1-(2',6'-dimethylphenyl)-3-(N-ethyl-N-methylamidino)urea hydrochloride
1-(2',6'-dimethylphenyl)-3-(N-ethyl-N'-methylamidino)urea hydrochloride
1-(2',6'-dimethylphenyl)-3-(N,N-dimethyl-N'-ethylamidino)urea hydrochloride
1-(2',6'-dimethylphenyl)-3-(N,N-diethyl-N'-methylamidino)urea hydrochloride
1-(2',6'-dimethylphenyl)-3-(N-methyl-N-propylamidino)urea hydrochloride
1-(2',6'-dimethylphenyl)-3-(N-methyl-N'-propylamidino)urea hydrochloride
1-(2',6'-dimethylphenyl)-3-(N-methyl-N-butylamidino)urea hydrochloride
1-(2',6'-dimethylphenyl)-3-(N-methyl-N'-butylamidino)urea hydrochloride
1-(2',6'-dimethylphenyl)-3-(N,N-dimethyl-N'-propylamidino)urea hydrochloride
1-(2',6'-dimethylphenyl)-3-(N,N-dimethyl-N-butylamidino)urea hydrochloride
1-(2',6'-dimethylphenyl)-3-(N,N-dipropylamidino)urea hydrochloride
1-(2',6'-dimethylphenyl)-3-(N,N-dipropylamidino)urea hydrochloride
1-(2',6'-dimethylphenyl)-3-(N,N'-dipropylamidino)urea hydrochloride
1-(2',6'-dimethylphenyl)-3-(N-ethyl-N-propylamidino)urea hydrochloride
1-(2',6'-dimethylphenyl)-3-(N'-ethyl-N-propylamidino)urea hydrochloride
1-(2',6'-dimethylphenyl)-3-(N'-methyl-N-pentylamidino)urea hydrochloride
1-(2',6'-dimethylphenyl)-3-(N'-methyl-N-hexylamidino)urea hydrochloride
1-(2',6'-dimethylphenyl)-3-(N'-methyl-N-heptylamidino)urea hydrochloride
1-(2',6'-dimethylphenyl)-3-(N'-methyl-N-allylamidino)urea hydrochloride
1-(2',6'-dimethylphenyl)-3-(N'-methyl-N-propargylamidino)urea hydrochloride
1-(2',6'-dimethylphenyl)-3-(N'-methyl-N-cyclopropylamidino)urea hydrochloride
1-(2',6'-dimethylphenyl)-3-(N'-methyl-N-(2-cyclopentenyl)amidino]urea HCl
1-(2',6'-dimethylphenyl)-3-(N'-methyl-N-cyclopropylmethylamidino)urea HCl
1-(2',6'-dimethylphenyl)-3-(N'-methyl-N-benzyloxyethylamidino)urea HCl
1-(2',6'-dimethylphenyl)-3-(N'-methyl-N-phenethoxyethylamidino)urea HCl
1-(2',6'-dimethylphenyl)-3-(N'-methyl-N-benzyloxypropylamidino)urea HCl
1-(2',6'-dimethylphenyl)-3-(N'-methyl-N-phenethoxypropylamidino)urea HCl
1-(2',6'-dimethylphenyl)-3-(N-methyl-N-benzyloxypropylamidino)urea HCl
1-(2',6'-dimethylphenyl)-3-(N-methyl-N-phenethoxyethylamidino)urea hydrochloride
1-(2',6'-dimethylphenyl)-3-(N-methyl-N-benzyloxyethylamidino)urea hydrochloride
1-(2',6'-dimethylphenyl)-3-(N,N'-dimethyl-N-benzyloxyethylamidino)urea HCl
1-(2',6'-dimethylphenyl)-3-(N'-methyl-N-benzylamidino)urea hydrochloride
1-(2',6'-dimethylphenyl)-3-(N'-methyl-N-phenethylamidino)urea hydrochloride
1-(2',6'-dimethylphenyl)-3-(N'-ethyl-N-bezyloxyethylamidino)urea hydrochloride
1-(2',6'-dimethylphenyl)-3-(N'-propyl-N-benzyloxyethylamidino)urea hydrochloride
1-(2',6'-dimethylphenyl)-3-(N,N-tetramethyleneamidino)urea hydrochloride
1-(2',6'-dimethylphenyl)-3-(N,N-pentamethyleneamidino)urea hydrochloride
1-(2',6'-dimethylphenyl)-3-(N,N-hexamethyleneamidino)urea hydrochloride
1-(2',6'-dimethylphenyl)-3-[N,N-(3'-oxapentamethylene)amidino]urea hydrochloride
1-(2',6'-dimethylphenyl)-3-[N,N-(3'-methyl-3'-azapentamethylene)amidino]urea HCl
1-(2',6'-dimethylphenyl)- 3-[N,N-(3'-methyl-3'-azahexamethylene)amidino]urea HCl
1-(2',6'-dimethylphenyl)-3-[N,N-(3'-thiapentamethylene)amidino]urea hydrochloride
1-(2',6'-dimethylphenyl)-3-[N,N-(2'-thiatetramethylene)amidino]urea hydrochloride
1-(2',6'-dimethylphenyl)-3-[N-(2'-butenyl)amidino]urea hydrochloride
1-(2',6'-dimethylphenyl)-3-[N-(2'-butynyl)amidino]urea hydrochloride
1-(2',6'-dimethylphenyl)-3-[N-(3'-butynyl)amidino]urea hydrochloride
1-(2',6'-dimethylphenyl)-3-(N-methyl-N-allylamidino)urea hydrochloride
1-(2',6'-dimethylphenyl)-3-(N-methyl-N-propargylamidino)urea hydrochloride
1-(2',6'-dimethylphenyl)-3-(N-methyl-N-cyclopropylamidino)urea hydrochloride
1-(2',6'-dimethylphenyl)-3-(N,N,N',N'-tetramethylamidino)urea hydrochloride
1-(2',6'-dimethylphenyl)-3-(N,N-dimethyl-N',N'-diethylamidino)urea hydrochloride
1-(2',6'-dimethylphenyl)-3-(N,N'-dimethyl-N,N'-diethylamidino)urea hydrochloride
1(2',6'-dimethylphenyl)-3-(N,N,N'-trimethyl-N'-ethylamidino)urea hydrochloride
1-(2',6'-dimethylphenyl)-3-(N,N,N',N'-tetraethylamidino)urea hydrochloride
1-(2',6'-dimethylphenyl)-3-(N,N,N',N'-tetrapropylamidino)urea hydrochloride
1-(2',6'dimethylphenyl)-3-(N,N,N',N'-tetrabutylamidino)urea hydrochloride
1-(2',6'-dimethylphenyl)-3-(N-methyl-N'-ethyl-N,N'-dipropylamindino)urea hydrochloride
1-(2',6'-dimethylphenyl)-3-(N,N-pentamethylene-N'-methylamidino)urea hydrochloride
1-(2',6'-dimethylphenyl)-3-(N,N-pentamethylene-N',N'-pentamethyleneamidino)urea hydrochloride
1-(2',6'L-dimethylphenyl)-3-(N,N-tetramethylene-N'-methylamidino)urea hydrochloride
1-(2',6'-dimethylphenyl)-3-(N,N-pentamethylene-N',N'-dimethylamidino)urea hydrochloride
1-(2',6'-dimethylphenyl)-3-(N,N-pentamethylene-N',N'-tetramethyleneamidino)urea hydrochloride
1-(2',6'-dimethylphenyl)-3-(N,N-pentamethylene-N'-methyl-N'-ethylamidino)urea hydrochloride
1-(2',6'-dimethylphenyl)-3-(N,N-tetrametylene-N'-allylamidino)urea hydrochloride 1-(2',6'-dimethylphenyl)-3-(N,N-tetramethylene-N'-benzyloxyethylamidino)urea hydrochloride
1(2',6'-dimethylphenyl)-3-(N,N-tetramethylene-N'-propargylamidino)urea hydrochloride
1-(2',6'-dimethylphenyl)-3-(N-methyl-N-propargyl-N'-pentylamidino)urea hydrochloride
1-(2',6'-dimethylphenyl)-3-(N,N-hexamethylene-N'-methylamidino)urea hydrochloride
1-(2',6'-dimethylphenyl)-3-(N,N-hexamethylene-N',N'-dimethylamidino)urea hydrochloride
1-(2',6'-dimethylphenyl)3-[N,N-(3'-oxapentamethylene)-N'-methylamidino]urea hydrochloride
1-(2',6'-dimethylphenyl)-3-[N,N-(3-methyl-3'-azahexamethylene)-N',N'-dimethylamidino]urea hydrochloride
1-(2',6'-dimethylphenyl)-3-[N,N-(3'-methyl-3'-azahexamethylene)-N',N'-tetramethyleneamidino]urea hydrochloride

EXAMPLE 3

When methylguanidine sulfate in Example 1 is replaced by
  methylguanidine hydrochloride
  methylguanidine hydrobromide
  methylguanidine carbonate or
  methylguanidine nitrate
then the same product is prepared.

When the guanidines of Table I, Example 2, are used in the procedure of Example 1 as a salt other than the sulfate, then the same product is obtained.

EXAMPLE 4

When methylguanidine sulfate in Example 1 is replaced by methylguanidine and the sodium hydroxide solution is eliminated from the reaction procedure, then the same product is prepared.

When the free base of the guanidines is used in Examples 2 and 3 and the sodium hydroxide solution is eliminated from the reaction procedure, then the same product is prepared.

EXAMPLE 5

When it is desired to obtain the free base of the resultant amidinourea by the procedures of Examples 1-4, then the final step for preparing the hydrochloride salt is eliminated.

When it is desired to obtain the resultant amidinourea in the form of a salt other than the hydrochloride then the corresponding acid would be used in the final step of the reaction in place of the hydrogen chloride.

EXAMPLE 6

When the procedure of Example 1 is followed and the anilines of Table I below are used with the various guanidines of Examples 1-4, then the corresponding substituted amidinoureas ae prepared. A representative list of the compounds so prepared is shown in Table II below.

TABLE I 2,3-dimethylaniline
2,4-dimethylaniline
2,5-dimethylaniline
3,4-dimethylaniline
3,5-dimethylaniline
2,3-diethylaniline
2,4-diethylaniline
2,5-diethylaniline
2,6-diethylaniline
3,4-diethylaniline
3,5-diethylaniline
2-methyl-4-ethylaniline
2-ethyl-4-methylaniline
2-methyl-6-ethylaniline
2-methyl-3-ethylaniline
2,6-diisopropylaniline
2-methyl-5-ethylaniline
3-methyl-4-ethylaniline
3-methyl-5-ethylaniline
2-ethyl-3-methylaniline
2-methyl-6-isopropylaniline
2-ethyl-5-methylaniline
3-ethyl-4-methylaniline
2-methyl-6-propylaniline
2-ethyl-6-propylaniline
2,6-dipropylaniline
2-methyl-6-i-propylaniline
2-methyl-6-butylaniline
2-ethyl-6-butylaniline
2-methyl-6-chloroaniline
2-methyl-6-fluoroaniline
2-methyl-6-bromoaniline
2-methyl-6-iodoaniline
2-methyl-6-methoxyaniline
2-methyl-6-ethoxyaniline
2-methyl-6-trifluoromethylaniline
2-methyl-6-nitroaniline
2-ethyl-6-chloroaniline
2-ethyl-6-fluoroaniline
2-ethyl-6-bromoaniline
2-ethyl-6-methoxyaniline
2-ethyl-6-ethoxyaniline
2-ethyl-6-trifluoromethylaniline
2-propyl-6-chloroaniline
2-propyl-6-fluoroaniline
2-propyl-6-bromoaniline
2-propyl-6-methoxyaniline
2-propyl-6-ethoxyaniline
2-i-propyl-6-chloroaniline
2-i-propyl-6-fluoroaniline
2-i-propyl-6-methoxyaniline
2-butyl-6-chloroaniline
2-methyl-3-chloroaniline
2-methyl-4-chloroaniline
2-methyl-5-chloroaniline
2,3-dichloroaniline
2,4-dichloroaniline
2,5-dichloroaniline
2,6-dichloroaniline
3,4-dichloroaniline
3,5-dichloroaniline
2-chloro-6-bromoaniline
2-chloro-3-methylaniline
2-chloro-4-methylaniline
2-chloro-5-methylaniline
2-chloro-5-fluoroaniline
2-chloro-5-bromoaniline
2-chloro-5-trifluoromethylaniline
2-fluoro-5-chloroaniline
2-chloro-6-fluoroaniline
2-bromo-6-fluoroaniline
2,6-difluoroaniline
2-methylaniline
2-ethylaniline
2-propylaniline
4-trifluoromethylaniline 3,4-dimethoxyaniline
3,4,5-trimethoxyaniline
2-trifluoromethylaniline
2-methyl-4-bromoaniline
2-methyl-4-fluoroaniline
2-ethyl-4-chloroaniline
2-ethyl-4-fluoroaniline
2-methyl-4-methoxyaniline
2-ethyl-4-methoxyaniline
2,4,6-trimethylaniline
2,4,6-triethylaniline
2,4-diethyl-6-methylaniline
2,6-diethyl-4-methylaniline
2-methyl-4-propyl-6-ethylaniline
2,4-dimethyl-6-ethylaniline
2,4-dimethyl-6-chloroaniline
2,4-dimethyl-6-bromoaniline
2,4-dimethyl-6-fluoroaniline
2,4-dimethyl-6-trifluoromethylaniline
2,4-dimethyl-6-nitroaniline
2,4-dimethyl-6-methoxyaniline
2,6-dimethyl-4-ethylaniline
2,6-dimethyl-4-chloroaniline
2,6-dimethyl-4-bromoaniline
2,6-dimethyl-4-fluoroaniline
2,6-dimethyl-4-nitroaniline
2,6-dimethyl-4-methoxyaniline
2,6-dimethyl-4-propylaniline
2-methyl-4,6-dichloroaniline
2-methyl-4,6-difluoroaniline
2-methyl-4-fluoro-6-bromoaniline
2-methyl-4-fluoro-6-chloroaniline
2-methyl-4-bromo-6-chloroaniline
2-methyl-4-chloro-6-fluoroaniline
2-methyl-4-chloro-6-bromoaniline
2-methyl-4-methoxy-6-chloroaniline
2-methyl-4-ethyl-6-chloroaniline
2-methyl-4-chloro-6-trifluoromethylaniline
2-methyl-4-trifluoromethyl-6-chloroaniline
2-ethyl-4,6-dichloroaniline
2-ethyl-4,6-difluoroaniline
2-ethyl-4-fluoro-6-bromoaniline
2-ethyl-4-fluoro-6-chloroaniline
2-ethyl-4-bromo-6-chloroaniline
2-ethyl-4-chloro-6-fluoroaniline
2-ethyl-4-chloro-6-bromoaniline
2,6-diethyl-4-chloroaniline
2,6-diethyl-4-bromoaniline
2,6-diethyl-4-fluoroaniline
2-nitroaniline
4-nitroaniline
2,6-dibromoaniline
2,6-diiodoaniline
2-methyl-6-iiodoaniline
4-hydroxy-2,6-dimethylaniline
4-hydroxy-2,6-diethylaniline
4-hydroxy-2-methylaniline
4-hydroxy-2-methyl-6-ethylaniline
4-benzyloxy-2,6-dimethylaniline
4-benzyloxy-2,6-diethylaniline
4-amino-2,6-diethylaniline
3-nitro-2,6-dimethylaniline
4-amino-2,6-dimethylaniline
3-bromo-2,6-dimethylaniline
3-cyano-2,6-dimethylaniline
4-amino-2-i-propylaniline
4-acetylamino-2-i-propylaniline
4-acetylamino-2,6-dimethylaniline
4-acetylamino-2,6-diethylaniline
2-isopropyl-4-acetylamino-6-ethylaniline
2-methyl-6-chloro-4-hydroxy
2-methyl-6-bromo-4-hydroxy
2-methyl-6-fluoro-4-hydroxy
2-ethyl-6-chloro-4-hydroxy
2-ethyl-6-bromo-4-hydroxy
2-ethyl-6-fluoro-4-hydroxy
2-methyl-6-chloro-4-amino
2-methyl-6-bromo-4-amino
2-methyl-6-fluoro-4-amino
2-ethyl-6-chloro-4-amino
2-ethyl-6-bromo-4-amino
2-ethyl-6-fluoro-4-fluoro-4-amino
2-methyl-6-chloro-4-acetylaminoanaline
2-methyl-6-bromo-4-acetylaminoanaline
2-methyl-6-fluoro-4-acetylaminoanaline
2-ethyl-6-chloro-4-acetylaminoanaline
2-ethyl-6-bromo-4-acetylaminoanaline
2-ethyl-6-fluoro-4-acetylaminoanaline

EXAMPLE 7

1-(2',6'-Dimethylphenyl)-1-methyl-3-methylamidinourea nitrate

A. 125 g. of 2,6 dimethyl aniline and 375 ml. of 88% formic acid are mixed in a 1 liter bomb with magnetic stirrer. The temperature (oil bath) is brought to 120° C. The bomb is kept at this temperature for 24 hours. The bomb is then allowed to cool to room temperature and stirring continued for 48 hours. The pressure is released and the mixture is poured into an 800 ml. ice with stirring. The mixture is filtered and the solid washed extensively with water and sucked dry and then dried in vacuo at 90°–95° to give N-formyl-2,6-dimethylaniline (m.p. 163°–164.5° C.).

B. A suspension of 125.6 g. of 2,6-dimethylformanilide in 1100 ml. of dry tetrahydrofuran is cooled to 0° C. in ice-methanol. To this with constant stirring is added dropwise over a period of 3 hours 1125 ml. of 0.96 M $BH_3$ in tetrahydrofuran. This is then allowed to warm gradually to room temperature and then heated slowly to reflux. Refluxing is maintained for 6 hours and then stirred at room temperature another 15 hours. The reaction mixture is then cooled in ice and acidified with 425 ml. of 6 N HCl. A white solid forms. The mixture is evaporated in vacuo and the water-solid slurry dissolved into 2 l. of water. The solution is made strongly alkaline (with cooling) with 50% NaOH and then extracted twice with ether (2 l.) The ether is then washed three times with 100 ml. portions of water and twice with 100 ml. portions of saturated sodium chloride solution. The ether is then dried over sodium sulfate, filtered, acidified with ethereal HCl while cooling. The white solid which forms is filtered, washed with ether and sucked dry. This is recrystallized from isopropanol:methanol to give N,2,6-trimethylaniline hydrochloride (m.p. 255-257 dec.)

C. Into a suspension of 121.1 g. (0.71 moles) of N,2,6-trimethylaniline hydrochloride in 1 l. of benzene at reflux is bubbled an excess of phosgene (0.175 ml. of liquid or 1.6 moles). After introduction of the phosgene, the mixture is refluxed for 1 hour and then 700 ml. of benzene removed by distillation at slightly reduced pressure. After the phosgene is gone the residue is triturated with hexane (300 ml.), filtered and dried to give 2,6-dimethylphenyl-N-methylcarbamoyl chloride (m.p. 79°–80° C.).

D. To a suspension of 12.21 g. (0.05 moles) of methyl guanidine sulfate in 110 ml. of tetrahydrofuran is added 8.0 g. (0.10 moles of sodium hydroxide) of 50% aqueous sodium hydroxide. After stirring for 1½ hours, 4.5 g. of sodium sulfate is slowly added and the mixture stirred an additional ½ hour. To the solution is added a solution of 9.88 g. (0.05 moles) of 2,6-dimethylphenyl-N-methylcarbamoyl chloride in 30 ml. of tetrahydrofuran. After stirring for 24 hours, the THF is removed in vacuo and the residue partitioned with chloroform/water. The oily residue is triturated with 300 ml. of hexane and 20 ml. benzene to give a white solid. This is dissolved in 50 ml. of 1:4 HNO₃ and warmed slightly over ½ hour, then cooled. The white solid which forms is filtered and air dried to obtain 1-(2',6'-dimethylphenyl)-1-methyl-3-methylamidinourea nitrate.

When formic acid in the above procedure is replaced by acetic acid, propionic acid, butyric acid or pentanoic acid then the products prepared are:

1-(2',6'-dimethylphenyl)-1-ethyl-3-methylamidinourea
1-(2'-6'-dimethylphenyl)-1-propyl-3-methylamidinourea
1-(2',6'-dimethylphenyl)-1-butyl-3-methylamidinourea
1-(2',6'-dimethylphenyl)-1-pentyl-3-methylamidinourea When methyl guanidine sulfate in the above procedure is replaced by the guanidines of Examples 2-4 then the corresponding amidinourea is prepared. A representative list of the compounds so prepared is shown in Table I below.

TABLE I 1-(2',6'-dimethylphenyl)-1-methyl-3-ethylamidinourea
1-(2',6'-dimethylphenyl)-1-methyl-3-propylamidinourea
1-(2',6'-dimethylphenyl)-1-methyl-3-i-propylamidinourea
1-(2',6'-dimethylphenyl)-1-methyl-3-butylamidinourea
1-(2',6'-dimethylphenyl)-1-methyl-3-allylamidinourea
1-(2',6'-dimethylphenyl)-1-methyl-3-propargylamidinourea
1-(2',6'-dimethylphenyl)-1-methyl-3-cyclopropylamidinourea
1-(2',6'-dimethylphenyl)-1-methyl-3-cyclobutylamidinourea
1-(2',6'-dimethylphenyl)-1-methyl-3-(3-cyclohexenylamidino)urea
1-(2',6'-dimethylphenyl)-1-methyl-3-cyclopropylmethylamidinourea
1-(2',6'-dimethylphenyl)-1-methyl-3-benzyloxyethylamidinourea
1-(2',6'-dimethylphenyl)-1-methyl-3-benzyloxypropylamidinourea
1-(2',6'-dimethylphenyl)-1-methyl-3-phenoxyethylamidinourea
1-(2',6'-dimethylphenyl)-1-methyl-3-benzylamidinourea
1-(2',6'-dimethylphenyl)-1-methyl-3-(N,N-dimethylamidino)urea
1-(2',6'-dimethylphenyl)-1-methyl-3-(N,N'-dimethylamidino)urea
1-(2',6'-dimethylphenyl)-1-methyl-3-(N,N,N'-trimethylamidino)urea
1-(2',6'-dimethylphenyl)-1-methyl-3-(N,N-diethylamidino)urea
1-(2',6'-dimethylphenyl)-1-methyl-3-(N-ethyl-N-methylamidino)urea
1-(2',6'-dimethylphenyl)-1-methyl-3-(N-ethyl-N'-methylamidino)urea
1-(2',6'-dimethylphenyl)-1-methyl-3-(N'-methyl-N-benzyloxyethylamidino)urea
1-(2',6'-dimethylphenyl)-1-methyl-3-(N'-methyl-N-allylamidino)urea
1-(2',6'-dimethylphenyl)-1-methyl-3-(N,N-pentamethyleneamidino)urea
1-(2',6'-dimethylphenyl)-1-ethyl-3-ethylamidinourea
1-(2',6'-dimethylphenyl)-1-ethyl-3-propylamidinourea
1-(2',6'-dimethylphenyl)-1-ethyl-3-i-propylamidinourea
1-(2',6'-dimethylphenyl)-1-ethyl-3-butylamidinourea
1-(2',6'-dimethylphenyl)-1-ethyl-3-t-butylamidinourea
1-(2',6'-dimethylphenyl)-1-ethyl-3-allylamidinourea
1-(2',6'-dimethylphenyl)-1-ethyl-3-propargylamidinourea
1-(2',6'-dimethylphenyl)-1-ethyl-3-cyclopropylamidinourea
1-(2',6'-dimethylphenyl)-1-ethyl-3-cyclohexylamidinourea
1-(2',6'-dimethylphenyl)-1-ethyl-3-[N-(3'-cyclopentenyl)amidino]urea
1-(2',6'-dimethylphenyl)-1-ethyl-3-cyclopropylmethylamidinourea
1-(2',6'-dimethylphenyl)-1-ethyl-3-cyclopropylethylamidinourea
1-(2',6'-dimethylphenyl)-1-ethyl-3-benzyloxyethylamidinourea
1-(2',6'-dimethylphenyl)-1-ethyl-3-benzyloxypropylamidinourea
1-(2',6'-dimethylphenyl)-1-ethyl-3-phenethoxymethylamidinourea
1-(2',6'-dimethylphenyl)-1-ethyl-3-phenethoxyethylamidinourea
1-(2',6'-dimethylphenyl)-1-ethyl-3-benzylamidinourea
1-(2',6'-dimethylphenyl)-1-ethyl-3-(N,N-dimethylamidino)urea
1-(2',6'-dimethylphenyl)-1-ethyl-3-(N,N'-dimethylamidino)urea
1-(2',6'-dimethylphenyl)-1-ethyl-3-(N,N,N'-trimethylamidino)urea
1-(2',6'-dimethylphenyl)-1-ethyl-3-(N,N-diethylamidino)urea
1-(2',6'-dimethylphenyl)-1-ethyl-3-(N,N,N'-triethylamidino)urea
1-(2',6'-dimethylphenyl)-1-ethyl-3-(N-ethyl-N-methylamidino)urea
1-(2',6'-dimethylphenyl)-1-ethyl-3-(N-ethyl-N'-methylamidino)urea
1-(2',6'-dimethylphenyl)-1-ethyl-3-(N-ethyl-N-propylamidino)urea
1-(2',6'-dimethylphenyl)-1-ethyl-3-(N-ethyl-N-allylamidino)urea
1-(2',6'-dimethylphenyl)-1-ethyl-3-(N-methyl-N-propargylamidino)urea
1-(2',6'-dimethylphenyl)-1-ethyl-3-(N-methyl-N-benzyloxyethylamidino)urea
1-(2',6'-dimethylphenyl)-1-ethyl-3-(N,N-tetramethyleneamidino)urea
1-(2',6'-dimethylphenyl)-1-ethyl-3-[N,N-(3'-oxapentamethylene)amidino]urea
1-(2',6'-dimethyl)-1-propyl-3-methylamidinourea
1-(2',6'-dimethylphenyl)-1-propyl-3-ethylamidinourea
1-(2',6'-dimethylphenyl)-1-propyl-3-propylamidinourea
1-(2',6'-dimethylphenyl)-1-propyl-3-allylamidinourea
1-(2',6'-dimethylphenyl)-1-propyl-3-propargylamidinourea 1-(2',6'-dimethylphenyl)-1-propyl-3-benzyloxyethylamidinourea
1-(2',6'-dimethylphenyl)-1-propyl-3-(N,N-dimethylamidino)urea
1-(2',6'-dimethylphenyl)-1-butyl-3-methylamidinourea
1-(2',6'-dimethylphenyl)-1-butyl-3-ethylamidinourea
1-(2',6'-dimethylphenyl)-1-pentyl-3-methylamidinourea
1-(2',6'-dimethylphenyl)-1-pentyl-3-ethylamidinourea
1-(2',6'-dimethylphenyl)-1-methyl-3-i-butylamidinourea
1-(2',6'-dimethylphenyl)-1-methyl-3-(2-butynyl-)amidinourea
1-(2',6'-dimethylphenyl)-1-methyl-3-cyclopentyl amidinourea
1-(2',6'-dimethylphenyl)-1-methyl-3-cyclohexyl amidinourea
1-(2',6'-dimethylphenyl)-1-methyl-3-pentyl amidinourea
1-(2',6'-dimethylphenyl)-1-methyl-3-hexyl amidinourea
1-(2',6'-dimethylphenyl)-1-methyl-3-butenyl amidinourea
1-(2',6'-dimethylphenyl)-1-methyl-3-pentenyl amidinourea
1-(2',6'-dimethylphenyl)-1-methyl-3-hexenyl amidinourea
1-(2',6'-dimethylphenyl)-1-methyl-3-(N,N-dimethyl-N'-ethylamidino)urea
1-(2',6'-dimethylphenyl)-1-methyl-3-(N,N-diethyl-N'-methylamidino)urea
1-(2',6'-dimethylphenyl)-1-methyl-3-(N-ethyl-N-methyl-N'-methylamidino)urea
1-(2',6'-dimethylphenyl)-1-methyl-3-(N,N-pentamethylene-N'-methylamidino)urea
1-(2',6'-dimethylphenyl)-1-ethyl-3-i-butylamidinourea
1-(2',6'-dimethylphenyl)-1-butyl-3-i-butylamidinourea
1-(2',6'-dimethylphenyl)-1-pentyl-3-i-butyl amidinourea
1-(2',6'-dimethylphenyl)-1-methyl-3-(N,N-dimethylamidino)urea
1-(2',6'-dimethylphenyl)-1-methyl-3-(N,N'-dimethylamidino)urea
1-(2',6'-dimethylphenyl)-1-methyl-3-(N,N,N'-trimethylamidino)urea
1-(2',6'-dimethylphenyl)-1-methyl-3-(N,N,N',N'-tetramethylamidino)urea
1-(2',6'-dimethylphenyl)-1-methyl-3-(N,N-pentamethylene-N,N-pentamethylene amidino)urea When 2,6-dimethylaniline in the above procedure is replaced by the anilines of example 6, then the corresponding product is obtained.

When the above procedure is followed using the anilines of Example 6 and the guanidines of Examples 2-4, then the corresponding product is obtained. A representative list of products so prepared are shown in Table II below.

TABLE II 1-(2',6'-diethylphenyl)-3-methylamidinourea
1-(2',6'-diethylphenyl)-1-methyl-3-methylamidinourea
1-(2',6'-diethylphenyl)-1-methyl-3-(N,N-dimethylamidino)urea
1-(2',6'-diethylphenyl)-1-methyl-3-(N,N'-dimethylamidino)urea
1-(2',6'-diethylphenyl)-1-methyl-3-(N,N,N'-trimethylamidino)urea
1-(2',6'-diethylphenyl)-3-(N,N'-dimethylamidino)urea
1-(2',6'-diethylphenyl)-3-(N,N,N'-trimethylamidino)urea
1-(2',6'-diethylphenyl)-3-(N,N,N',N'-tetramethylamidino)urea
1-(2',6'-diethylphenyl)-1-methyl-3-(N,N,N',N'-tetramethylamidino)urea
1-(2',6'-diethylphenyl)-3-ethylamidinourea
1-(2',6'-diethylphenyl)-3-propylamidinourea
1-(2',6'-diethylphenyl)-3-i-propylamidinourea
1-(2',6'-diethylphenyl)-3-butylamidinourea
1-(2',6'-diethylphenyl)-3-i-butylamidinourea
1-(2',6'-diethylphenyl)-3-pentylamidinourea
1-(2',6'-diethylphenyl)-3-allylamidinourea
1-(2',6'-diethylphenyl)-3-propargylamidinourea
1-(2',6'-diethylphenyl)-3-cyclopropylamidinourea
1-(2',6'-diethylphenyl)-3-methoxyethylamidinourea
1-(2',6'-diethylphenyl)-3-benzyloxyethylamidinourea
1-(2',6'-diethylphenyl)-3-penethoxyethylamidinourea
1-(2',6'-diethylphenyl)-3-benzylamidinourea
1-(2',6'-diethylphenyl)-3-(N,N-dimethylamidino)urea
1-(2',6'-diethylphenyl)-3-(N,N'-dimethylamidino)urea
1-(2',6'-diethylphenyl)-3-(N,N-diethylamidino)urea
1-(2',6'-diethylphenyl)-3-(N,N'-diethylamidino)urea
1-(2',6'-diethylphenyl)-3-(N-ethyl-N'-methylamidino)urea
1-(2',6'-diethylphenyl)-3-(N'-methyl-N-benzyloxyethylamidino)urea
1-(2',6'-diethylphenyl)-3-(N,N-tetramethyleneamidino)urea
1-(2',6'-diethylphenyl)-3-(N,N-pentamethyleneamidino)urea
1-(2',6'-diethylphenyl)-3-(N-methyl-N'-propargylamidino)urea
1-(2',6'-diethylphenyl)-3-(N,N-tetramethylene-N'-allylamidino)urea
1-(2',6'-diethylphenyl)-3-(N,N-tetramethylene,N',N'-tetramethyleneamidino)urea
1-(2',6'-diethylphenyl)-1-methyl-3-ethylamidinourea
1-(2',6'-diethylphenyl)-1-methyl-3-propylamidinourea
1-(2',6'-diethylphenyl)-1-methyl-3-i-propylamidinourea
1-(2',6'-diethylphenyl)-1-methyl-3-butylamidinourea
1-(2',6'-diethylphenyl)-1-methyl-3-i-butylamidinourea
1-(2',6'-diethylphenyl)-1-methyl-3-allylamidinourea
1-(2',6'-diethylphenyl)-1-methyl-3-propargylamidinourea
1-(2',6'-diethylphenyl)-1-methyl-3-methoxyethylamidinourea
1-(2',6'-diethylphenyl)-1-methyl-3-benzyloxyethylamidinourea
1-(2',6'-diethylphenyl)-1-methyl-3-phenoxyethylamidinourea
1-(2',6'-diethylphenyl)-1-methyl-3-(N,N-diethylamidino)urea
1-(2',6'-diethylphenyl)-1-methyl-3-(N'-methyl-N-benzyloxyethylamidino)urea
1-(2',6'-diethylphenyl)-1-methyl-3-(N,N-pentamethyleneamidino)urea
1-(2',6'-diethylphenyl)-1-methyl-3-(N,N,N'-trimethylamidino)urea
1-(2',6'-diethylphenyl)-1-methyl-3-(N,N,N'-triethylamidino)urea
1-(2',6'-diethylphenyl)-1-methyl-3-(N,N,N',N'-tetraethylamidino)urea
1-(2',6'-diethylphenyl)-1-ethyl-3-methylamidinourea
1-(2',6'-diethylphenyl)-1-ethyl-3-methylamidinourea
1-(2',6'-diethylphenyl)-1-ethyl-3-propylamidinourea
1-(2',6'-diethylphenyl)-1-ethyl-3-butylamidinourea
1-(2',6'-diethylphenyl)-1-ethyl-3-i-butylamidinourea
1-(2',6'-diethylphenyl)-1-ethyl-3-(N,N-diethylamidino)urea
1-(2',6'-diethylphenyl)-1-ethyl-3-(N,N'-diethylamidino)urea 1-(2',6'-diethylphenyl)-1-ethyl-3-(N,N,N'-triethylamidino)urea
1-(2',6'-diethylphenyl)-1-ethyl-3-(N,N,N',N',-tetraethylamidino)urea
1-(2',6'-diethylphenyl)-1-ethyl-3-allylamidinourea
1-(2',6'-diethylphenyl)-1-ethyl-3-propargylamidinourea
1-(2',6'-diethylphenyl)-1-ethyl-3-methoxyethylamidinourea
1-(2',6'-diethylphenyl)-1-ethyl-3-benzyloxyethylamidinourea
1-(2',6'-diethylphenyl)-1-ethyl-3-phenethoxyethylamidinourea
1-(2',6'-diethylphenyl)-1-propyl-3-methylamidinourea
1-(2',6'-diethylphenyl)-1-propyl-3-ethylamidinourea
1-(2',6'-diethylphenyl)-1-propyl-3-propylamidinourea
1-(2',6'-diethylphenyl)-1-propyl-3-butylamidinourea
1-(2',6'-diethylphenyl)-1-propyl-3-i-butylamidinourea
1-(2',6'-diethylphenyl)-1-propyl-3-(N,N-dimethylamidino)urea
1-(2',6'-diethylphenyl)-1-propyl-3-(N,N,N'-trimethylamidino)urea
1-(2',6'-diethylphenyl)-1-propyl-3-allylamidinourea
1-(2',6'-diethylphenyl)-1-propyl-3-propargylamidinourea
1-(2',6'-diethylphenyl)-1-propyl-3-methoxyethylamidinourea
1-(2',6'-diethylphenyl)-1-propyl-3-benzyloxyethylamidinourea
1-(2',6'-diethylphenyl)-1-butyl-3-methylamidinourea
1-(2'-methyl-6'-ethylphenyl)-3-methylamidinourea
1-(2'-methyl-6'-ethylphenyl)-3-ethylamidinourea
1-(2'-methyl-6'-ethylphenyl)-3-propylamidinourea
1-(2'-methyl-6'-ethylphenyl)-3-i-propylamidinourea
1-(2'-methyl-6'-ethylphenyl)-3-butylamidinourea
1-(2'-methyl-6'-ethylphenyl)-3-i-butylamidinourea
1-(2'-methyl-6'-ethylphenyl)-3-t-butylamidinourea
1-(2'-methyl-6'-ethylphenyl)-3-pentylamidinourea
1-(2'-methyl-6'-ethylphenyl)-3-allylamidinourea
1-(2'-methyl-6'-ethylphenyl)-3-propargylamidinourea
1-(2'-methyl-6'-ethylphenyl)-3-cyclopropylamidinourea
1-(2'-methyl-6'-ethylphenyl)-3-cyclobutylamidinourea
1-(2'-methyl-6'-ethylphenyl)-3-[N-(3'-cyclopentenyl)amidino]urea
1-(2'-methyl-6'-ethylphenyl)-3-cyclopropylmethylamidinourea
1-(2'-methyl-6'-ethylphenyl)-3-cyclobutylethylamidinourea
1-(2'-methyl-6'-ethylphenyl)-3-methoxyethylamidinourea
1-(2'-methyl-6'-ethylphenyl)-3-benzyloxyethylamidinourea
1-(2'-methyl-6'-ethylphenyl)-3-phenethoxyethylamidinourea
1-(2'-methyl-6'-ethylphenyl)-3-benzylamidinourea
1-(2'-methyl-6'-ethylphenyl)-3-(N,N-dimethylamidino)urea
1-(2'-methyl-6'-ethylphenyl)-3-(N,N'-dimethylamidino)urea
1-(2'-methyl-6'-ethylphenyl)-3-(N,N,N'-trimethylamidino)urea
1-(2'-methyl-6'-ethylphenyl)-3-(N,N,N,N'-tetramethylamidino)urea
1-(2'-methyl-6'-ethylphenyl)-3-(N,N-diethylamidino)urea
1-(2'-methyl-6'-ethylphenyl)-3-(N,N'-diethylamidino)urea
1-(2'-methyl-6'-ethylphenyl)-3-(N-methyl-N'-ethylamidino)urea
1-(2'-methyl-6'-ethylphenyl)-3-(N-methyl-N'-benzyloxyethylamidino)urea
1-(2'-methyl-6'-ethylphenyl)-3-(N,N-tetramethyleneamidino)urea
1-(2'-methyl-6'-ethylphenyl)-3-(N,N-tetramethylene-N',N'-tetramethyleneamidino)urea
1-(2'-methyl-6'-ethylphenyl)-3-[N,N(3'-methyl-3'-azapentamethylene)amidino]urea
1-(2'-methyl-6'-ethylphenyl)-3-[N,N-(3'-oxapentamethylene)amidino]urea
1-(2'-methyl-6'-ethylphenyl)-1-methyl-3-methylamidinourea
1-(2'-methyl-6'-ethylphenyl)-1-methyl-3-ethylamidinourea
1-(2'-methyl-6'-ethylphenyl)-1-methyl-3-propylamidinourea
1-(2'-methyl-6'-ethylphenyl)-1-methyl-3-i-propylamidinourea
1-(2'-methyl-6'-ethylphenyl)-1-methyl-3-butylamidinourea
1-(2'-methyl-6'-ethylphenyl)-1-methyl-3-i-butylamidinourea
1-(2'-methyl-6'-ethylphenyl)-1-methyl-3-t-butylamidinourea
1-(2'-methyl-6'-ethylphenyl)-1-methyl-3-allylamidonourea
1-(2'-methyl-6'-ethylphenyl)-1-methyl-3-propargylamidinourea
1-(2'-methyl-6'-ethylphenyl)-1-methyl-3-methoxyethylamidinourea
1-(2'-methyl-6'-ethylphenyl)-1-methyl-3-benzyloxyethylamidinourea
1-(2'-methyl-6'-ethylphenyl)-1-methyl-3-phenethoxyethylamidinourea
1-(2'-methyl-6'-ethylphenzl)-1-methyl-3-(N,N-dimethylamidino)urea
1-(2'-methyl-6'-ethylphenyl)-1-methyl-3-(N,N-diethylamidino)urea
1-(2'-methyl-6'-ethylphenyl)-1-methyl-3-(N,N'-dimethylamidino)urea
1-(2'-methyl-6'-ethylphenyl)-1-methyl-3-(N-methyl-N'-ethylamidino)urea
1-(2'-methyl-6'-ethylphenyl)-1-methyl-3-(N-ethyl-N'-benzyloxyethylamidino)urea
1-(2'-methyl-6'-ethylphenyl)-1-methyl-3-(N-ethyl-N'-allylamidino)urea
1-(2'-methyl-6'-ethylphenyl)-1-methyl-3-(N-ethyl-N'-propargylamidino)urea
1-(2'-methyl-6'-ethylphenyl)-1-methyl-3-(N,N-tetramethyleneamidino)urea
1-(2'-methyl-6'-ethylphenyl)-1-methyl-3-(N,N,N'-trimethylamidino)urea
1-(2'-methyl-6'-ethylphenyl)-1-methyl-3-(N,N,N,N'-tetramethylamidino)urea
1-(2'-methyl-6'-ethylphenyl)-1-ethyl-3-methylamidinourea
1-(2'-methyl-6'-ethylphenyl)-1-ethyl-3-ethylamidinourea
1-(2'-methyl-6'-ethylphenyl)-1-ethyl-3-propylamidinourea
1-(2'-methyl-6'-ethylphenyl)-1-ethyl-3-butylamidinourea
1-(2'-methyl-6'-ethylphenyl)-1-ethyl-3-i-butylamidinourea
1-(2'-methyl-6'-ethylphenyl)-1-ethyl-3-(N,N-dimethylamidino)urea
1-(2'-methyl-6'-ethylphenyl)-1-ethyl-3-(N,N'-dimethylamidino)urea 1-(2'-methyl-6'-ethylphenyl)-1-ethyl-3-(N,N-diethylamidino)urea
1-(2'-methyl-6'-ethylphenyl)-1-ethyl-3-(N',N,N'-trimethylamidino)urea
1-(2'-methyl-6'-ethylphenyl)-1-ethyl-3-allylamidinourea
1-(2'-methyl-6'-ethylphenyl)-1-ethyl-3-propargylamidinourea
1-(2'-methyl-6'-ethylphenyl)-1-ethyl-3-methoxyethylamidinourea
1-(2'-methyl-6'-ethylphenyl)-1-ethyl-3-benzyloxyethylamidinourea
1-(2'-methyl-6'-ethylphenyl)-1-ethyl-3-pheneoxyethylamidinourea
1-(2'-methyl-6'-ethylphenyl)-1-ethyl-3-(N-methyl-N'-allylamidino)urea
1-(2'-methyl-6'-ethylphenyl)-1-ethyl-3-(N-ethyl-N'-benzyloxyethylamidino)urea
1-(2'-methyl-6'-chlorophenyl)-3-methylamidinourea
1-(2'-methyl-6'-chlorophenyl)-3-ethylamidinourea
1-(2'-methyl-6'-chlorophenyl)-3-propylamidinourea
1-(2'-methyl-6'-chlorophenyl)-3-i-propylamidinourea
1-(2'-methyl-6'-chlorophenyl)-3-butylamidinourea
1-(2'-methyl-6'-chlorophenyl)-3-i-butylamidinourea
1-(2'-methyl-6'-chlorophenyl)-3-t-butylamidinourea
1-(2'-methyl-6'-chlorophenyl)-3-pentylamidinourea
1-(2'-methyl-6'-chlorophenyl)-3-allylamidinourea
1-(2'-methyl-6'-chlorophenyl)-3-propargylamidinourea
1-(2'-methyl-6'-chlorophenyl)-3-cyclobutylamidinourea
1-(2'-methyl-6'-chlorophenyl)-3-cyclohexylamidinourea
1-(2'-methyl-6'-chlorophenyl)-3-benzylamidinourea
1-(2'-methyl-6'-chlorophenyl)-3-methoxyethylamidinourea
1-(2'-methyl-6'-chlorophenyl)-3-benzyloxyethylamidinourea
1-(2'-methyl-6'-chlorophenyl)-3-phenethoxyethylamidinourea
1-(2'-methyl-6'-chlorophenyl)-3-(N,N-dimethylamidino)urea
1-(2'-methyl-6'-chlorophenyl)-3-(N,N'-dimethylamidino)urea
1-(2'-methyl-6'-chlorophenyl)-3-(N,N-diethylamidino)urea
1-(2'-methyl-6'-chlorophenyl)-3-(N,N'-diethylamidino)urea
1-(2'-methyl-6'-chlorophenyl)-3-(N-ethyl-N'-methylamidino)urea 1-(2'-methyl-6'-chlorophenyl)-3-(N-methyl-N'-allylamidino)urea
1-(2''-methyl-6'-chlorophenyl)-3-(N-methyl-N'-propargylamidino)urea
1-(2'-methyl-6'-chlorophenyl)-3-(N-ethyl-N'-benzyloxyethylamidino)urea
1-(2'-methyl-6'-chlorophenyl)-3-(N-propyl-N'-allylamidino)urea
1-(2'-methyl-6'-chlorophenyl)-3-(N,N-pentamethyleneamidino)urea
1-(2'-methyl-6'-chlorophenyl)-3-(N,N-tetramethylene-N'-methylamidino)urea
1-(2'-methyl-6'-chlorophenyl)-3-(N,N,N'-trimethylamidino)urea
1-(2'-methyl-6'-chlorophenyl)-3-(N,N,N',N'-tetramethylamidino)urea
1-(2'-methyl-6'-chlorophenyl)-3-(N,N-tetramethylene-N',N'-tetramethylene amidino)urea
1-(2'-methyl-6'-chlorophenyl)-1-methyl-3-methylamidinourea
1-(2'-methyl-6'-chlorophenyl)-1-methyl-3-ethylamidinourea
1-(2'-methyl-6'-chlorophenyl)-1-methyl-3-propylamidinourea
1-(2'-methyl-6'-chlorophenyl)-1-methyl-3-i-propylamidinourea
1-(2'-methyl-6'-chlorophenyl)-1-methyl-3-butylamidinourea
1-(2'-methyl-6'-chlorophenyl)-1-methyl-3-i-butylamidinourea
1-(2'-methyl-6'-chlorophenyl)-1-methyl-3-t-butylamidinourea
1-(2'-methyl-6'-chlorophenyl)-1-methyl-3-pentylamidinourea
1-(2'-methyl-6'-chlorophenyl)-1-methyl-3-hexylamidinourea
1-(2'-methyl-6'-chlorophenyl)-1-methyl-3-heptylamidinourea
1-(2'-methyl-6'-chlorophenyl)-1-methyl-3-allylamidinourea
1-(2'-methyl-6'-chlorophenyl)-1-methyl-3-propargylamidinourea
1-(2'-methyl-6'-chlorophenyl)-1-methyl-3-methoxyethylamidinourea
1-(2'-methyl-6'-chlorophenyl)-1-methyl-3-benzyloxyethylamidinourea
1-(2'-methyl-6'-chlorophenyl)-1-methyl-3-phenethoxyethylamidinourea
1-(2'-methyl-6'-chlorophenyl)-1-methyl-3-benzylamidinourea
1-(2'-methyl-6'-chlorophenyl)-1-methyl-3-(N,N-dimethylamidino)urea
1-(2'-methyl-6'-chlorophenyl)-1-methyl-3-(N,N'-dimethylamidino)urea
1-(2'-methyl-6'-chlorophenyl)-1-methyl-3-(N,N-diethylamidino)urea
1-(2'-methyl-6'-chlorophenyl)-1-methyl-3-(N,N'-diethylamidino)urea
1-(2'-methyl-6'-chlorophenyl)-1-methyl-3-(N-methyl-N'-ethylamidino)urea
1-(2'-methyl-6'-chlorophenyl)-1-methyl-3-(N'-methyl-N-benzyloxyethylamidino)urea 1-(2'-methyl-6'-chlorophenyl)-1-methyl-3-(N'-allyl-N-methylamidino)urea
1-(2'-methyl-6'-chlorophenyl)-1-methyl-3-(N'-propargyl-N-methylamidino)urea
1-(2'-methyl-6'-chlorophenyl)-1-methyl-3-(N,N-tetramethyleneamidino)urea
1-(2'-methyl-6'-chlorophenyl)-1-methyl-3-(N,N,N'-trimethylamidino)urea
1-(2'-methyl-6'-chlorophenyl)-1-methyl-3-(N,N,N',N'-tetramethylamidino)urea
1-(2'-methyl-6'-chlorophenyl)-1-ethyl-3-methylamidinourea
1-(2'-methyl-6'-chlorophenyl)-1-ethyl-3-ethylamidinourea
1-(2'-methyl-6'-chlorophenyl)-1-ethyl-3-propylamidinourea
1-(2'-methyl-6'-chlorophenyl)-1-ethyl-3-i-propylamidinourea
1-(2'-methyl-6'-chlorophenyl)-1-ethyl-3-butylamidinourea
1-(2'-methyl-6'-chlorophenyl)-1-ethyl-3-i-butylamidinourea
1-(2'-methyl-6'-chlorophenyl)-1-ethyl-3-t-butylamidinourea
1-(2'-methyl-6'-chlorophenyl)-1-ethyl-3-methoxyethylamidinourea
1-(2'-methyl-6'-chlorophenyl)-1-ethyl-3-benzyloxyethylamidinourea 1-(2'-methyl-6'-chlorophenyl)-1-ethyl-3-allylamidinourea
1-(2'-methyl-6'-chlorophenyl)-1-ethyl-3-propargylamidinourea
1-(2'-methyl-6'-chlorophenyl)-1-ethyl-3-(N,N-dimethylamidino)urea
1-(2'-methyl-6'-chlorophenyl)-1-ethyl-3-(N,N'-dimethylamidino)urea
1-(2'-methyl-6'-chlorophenyl)-1-ethyl-3-(N,N-diethylamidino)urea
1-(2'-methyl-6'-chlorophenyl)-1-ethyl-3-(N,N'-diethylamidino)urea
1-(2'-methyl-6'-chlorophenyl)-1-ethyl-3-(N,N,N'-trimethylamidino)urea
1-(2'-methyl-6'-chlorophenyl)-1-ethyl-3-(N,N,N',N'-tetramethylamidino)urea
1-(2'-methyl-6'-chlorophenyl)-1-ethyl-3-(N,N-tetramethyleneamidino)urea
1-(2'-methyl-6'-chlorophenyl)-1-propyl-3-methylamidinourea
1-(2'-methyl-6'-chlorophenyl)-1-propyl-3-ethylamidinourea
1-(2'-methyl-6'-bromophenyl)-3-methylamidinourea
1-(2'-methyl-6'-bromophenyl)-3-ethylamidinourea
1-(2'-methyl-6'-bromophenyl)-3-propylamidinourea
1-(2'-methyl-6'-bromophenyl)-3-i-propylamidinourea
1-(2'-methyl-6'-bromophenyl)-3-butylamidinourea
1-(2'-methyl-6'-bromophenyl)-3-i-butylamidinourea
1-(2'-methyl-6'-bromophenyl)-3-t-butylamidinourea
1-(2'-methyl-6'-bromophenyl)-3-pentylamidinourea
1-(2'-methyl-6'-bromophenyl)-3-hexylamidinourea
1-(2'-methyl-6'-bromophenyl)-3-propargylamidinourea
1-(2'-methyl-6'-bromophenyl)-3-allylamidinourea
1-(2'-methyl-6'-bromophenyl)-3-methoxyethylamidinourea
1-(2'-methyl-6'-bromophenyl)-3-benzyloxyethylamidinourea
1-(2'-methyl-6'-bromophenyl)-3-phenethoxyethylamidinourea
1-(2'-methyl-6'-bromophenyl)-3-(N,N-dimethylamidino)urea
1-(2'-methyl-6'-bromophenyl)-3-(N,N'-dimethylamidino)urea
1-(2'-methyl-6'-bromophenyl)-3-(N,N-diethylamidino)urea
1-(2'-methyl-6'-bromophenyl)-3-(N,N'-diethylamidino)urea
1-(2'-methyl-6'-bromophenyl)-3-(N-methyl-N'-ethylamidino)urea
1-(2'-methyl-6'-bromophenyl)-3-(N-methyl-N-ethylamidino)urea
1-(2'-methyl-6'-bromophenyl)-3-(N,N-tetramethyleneamidino)urea
1-(2'-methyl-6'-bromophenyl)-3-(N,N-pentamethyleneamidino)urea
1-(2'-methyl-6'-bromophenyl)-3-(N,N-hexamethyleneamidino)urea
1-(2'-methyl-6'-bromophenyl)-3-(N,N,N',N'-tetramethylamidino)urea
1-(2'-methyl-6'-bromophenyl)-3-(N,N,N'-trimethylamidino)urea
1-(2'-methyl-6'-bromophenyl)-1-methyl-3-methylamidinourea
1-(2'-methyl-6'-bromophenyl)-1-methyl-3-ethylamidinourea
1-(2'-methyl-6'-bromophenyl)-1-methyl-3-propylamidinourea
1-(2'-methyl-6'-bromophenyl)-1-methyl-3-i-propylamidinourea
1-(2'-methyl-6'-bromophenyl)-1-methyl-3-butylamidinourea
1-(2'-methyl-6'-bromophenyl)-1-methyl-3-i-butylamidinourea
1-(2'-methyl-6'-bromophenyl)-1-methyl-3-allylamidinourea
1-(2'-methyl-6'-bromophenyl)-1-methyl-3-propargylamidinourea
1-(2'-methyl-6'-bromophenyl)-1-methyl-3-methoxyethylamidinourea
1-(2'-methyl-6'-bromophenyl)-1-methyl-3-benzyloxyethylamidinourea
1-(2'-methyl-6'-bromophenyl)-1-methyl-3-phenethoxyethylamidinourea
1-(2'-methyl-6'-bromophenyl)-1-methyl-3-(N,N-dimethylamidino)urea
1-(2'-methyl-6'-bromophenyl)-1-methyl-3-(N,N'-dimethylamidino)urea
1-(2'-methyl-6'-bromophenyl)-1-methyl-3-(N,N-diethylamidino)urea
1-(2'-methyl-6'-bromophenyl)-1-methyl-3-(N,N'-diethylamidino)urea
1-(2'-methyl-6'-bromophenyl)-1-methyl-3-(N,N,N'-trimethylamidino)urea
1-(2'-methyl-6'-bromophenyl)-1-methyl-3-(N-methyl-N'-ethylamidino)urea
1-(2'-methyl-6'-bromophenyl)-1-methyl-3-(N,N-tetramethyleneamidino)urea
1-(2'-methyl-6'-bromophenyl)-1-methyl-3-(N,N-pentamethyleneamidino)urea
1-(2'-methyl-6'-bromophenyl)-1-ethyl-3-methylamidinourea
1-(2'-methyl-6'-bromophenyl)-1-ethyl-3-ethylamidinourea
1-(2'-methyl-6'-bromophenyl)-1-ethyl-3-propylamidinourea
1-(2'-methyl-6'-bromophenyl)-1-ethyl-3-i-butylamidinourea
1-(2'-methyl-6'-bromophenyl)-1-ethyl-3-allylamidinourea
1-(2'-methyl-6'-bromophenyl)-1-ethyl-3-propargylamidinourea
1-(2'-methyl-6'-bromophenyl)-1-ethyl-3-methoxyethylamidinourea
1-(2'-methyl-6'-bromophenyl)-1-ethyl-3-benzyloxyethylamidinourea
1-(2'-methyl-6'-bromophenyl)-1-ethyl-3-(N,N-dimethylamidino)urea
1-(2'-methyl-6'-bromophenyl)-1-ethyl-3-(N,N-pentamethyleneamidino)urea
1-(2'-methyl-6'-bromophenyl)-1-ethyl-3-(N,N,N'-trimethylamidino)urea
1-(2'-methyl-6'-bromophenyl)-1-propyl-3-methylamidinourea
1-(2'-methyl-6'-bromophenyl)-1-propyl-3-ethylamidinourea
1-(2'-methyl-6'-bromophenyl)-1-propyl-3-propylamidinourea
1-(2'-methyl-6'-bromophenyl)-1-propyl-3-(N,N-dimethylamidino)urea
1-(2'-methyl-6'-bromophenyl)-1-propyl-3-(N,N-tetramethyleneamidino)urea
1-(2'-methyl-6'-bromophenyl)-1-propyl-3-(N,N,N'-trimethylamidino)urea
1-(2'-ethyl-6'-chlorophenyl)-3-methylamidinourea
1-(2'-ethyl-6'-chlorophenyl)-3-ethylamidinourea 1-(2'-ethyl-6'-chlorophenyl)-3-propylamidinourea
1-(2'-ethyl-6'-chlorophenyl)-3-butylamidinourea
1-(2'-ethyl-6'-chlorophenyl)-3-i-butylamidinourea
1-(2'-ethyl-6'-chlorophenyl)-3-pentylamidinourea
1-(2'-ethyl-6'-chlorophenyl)-3-allylamidinourea
1-(2'-ethyl-6'-chlorophenyl)-3-propargylamidinourea
1-(2'-ethyl-6'-chlorophenyl)-3-methoxyethylamidinourea
1(2'-ethyl-6'-chlorophenyl)-3-benzyloxyethylamidinourea
1-(2'-ethyl-6'-chlorophenyl)-3-(N,N-dimethylamidino)urea
1-(2'-ethyl-6'-chlorophenyl)-3-(N,N'-dimethylamidino)urea
1-(2'-ethyl-6'-chlorophenyl)-3-(N,N-diethylamidino)urea
1-(2'-ethyl-6'-chlorophenyl)-3-(N,N'-diethylamidino)urea
1-(2'-ethyl-6'-chlorophenyl)-3-(N,N-tetramethyleneamidino)urea
1-(2'-ethyl-6'-chlorophenyl)-3-(N,N-tetramethylene-N'-methylamidino)urea
1-(2'-ethyl-6'-chlorophenyl)-3-(N,N,N'-trimethylamidino)urea
1-(2'-ethyl-6'-chlorophenyl)-3-(N,N,N',N'-tetramethylamidino)urea
1-(2'-ethyl-6'-chlorophenyl)-1-methyl-3-methylamidinourea
1-(2'-ethyl-6'-chlorophenyl)-1-methyl-3-ethylamidinourea
1-(2'-ethyl-6'-chlorophenyl)-1-methyl-3-propylamidinourea
1-(2'-ethyl-6'-chlorophenyl)-1-methyl-3-butylamidinourea
1-(2'-ethyl-6'-chlorophenyl)-1-methyl-3-i-butylamidinourea
1-(2'-ethyl-6'-chlorophenyl)-1-methyl-3-pentylamidinourea
1-(2'-ethyl-6'-chlorophenyl)-1-methyl-3-allylamidinourea
1-(2'-ethyl-6'-chlorophenyl)-1-methyl-3-propargylamidinourea
1-(2'-ethyl-6'-chlorophenyl)-1-methyl-3-methoxyethylamidinourea
1-(2'-ethyl-6'-chlorophenyl)-1-methyl-3-benzyloxyethylamidinourea
1-(2'-ethyl-6'-chlorophenyl)-1-methyl-3-(N,N-dimethylamidino)urea
1-(2'-ethyl-6'-chlorophenyl)-1-methyl-3-(N,N'-dimethylamidino)urea
1-(2'-ethyl-6'-chlorophenyl)-1-methyl-3-(N,N-diethylamidino)urea
1-(2'-ethyl-6'-chlorophenyl)-1-methyl-3-(N,N'-diethylamidino)urea
1-(2'-ethyl-6'-chlorophenyl)-1-methyl-3-(N,N-tetramethyleneamidino)urea
1-(2'-ethyl-6'-chlorophenyl)-1-methyl-3-(N,N-tetramethylene-N'-methylamidino)urea
1-(2'-ethyl-6'-chlorophenyl)-1-methyl-3-(N,N,N',N'-tetramethylamidino)urea
1-(2'-ethyl-6'-chlorophenyl)-1-methyl-3-(N,N,N'-trimethylamidino)urea
1-(2'-ethyl-6'-chlorophenyl)-1-ethyl-3-methylamidinourea
1-(2'-ethyl-6'-chlorophenyl)-1-ethyl-3-ethylamidinourea
1-(2'-ethyl-6'-chlorophenyl)-1-ethyl-3-propylamidinourea
1-(2'-ethyl-6'-chlorophenyl)-1-ethyl-3-i-propylamidinourea
1-(2'-ethyl-6'-chlorophenyl)-1-ethyl-3-butylamidinourea
1-(2'-ethyl-6'-chlorophenyl)-1-ethyl-3-i-butylamidinourea
1-(2'-ethyl-6'-chlorophenyl)-1-ethyl-3-t-butylamidinourea
1-(2'-ethyl-6'-chlorophenyl)-1-ethyl-3-allylamidinourea
1-(2'-ethyl-6'-chlorophenyl)-1-ethyl-3-propargylamidinourea
1-(2'-ethyl-6'-chlorophenyl)-1-ethyl-3-cyclopropylamidinourea
1-(2'-ethyl-6'-chlorophenyl)-1-ethyl-3-methoxyethylamidinourea
1-(2'-ethyl-6'-chlorophenyl)-1-ethyl-3-benzyloxyethylamidinourea
1-(2'-ethyl-6'-chlorophenyl)-1-ethyl-3-(N,N-dimethylamidino)urea
1-(2'-ethyl-6'-chlorophenyl)-1-ethyl-3-(N,N'-dimethylamidino)urea
1-(2'-ethyl-6'-chlorophenyl)-1-ethyl-3-(N,N-diethylamidino)urea
1-(2'-ethyl-6'-chlorophenyl)-1-ethyl-3-(N,N'-diethylamidino)urea
1-(2'-ethyl-6'-chlorophenyl)-1-ethyl-3-(N-methyl-N'-ethylamidino)urea
1-(2'-ethyl-6'-chlorophenyl)-1-ethyl-3-(N,N,N'-trimethylamidino)urea
1-(2'-ethyl-6'-chlorophenyl)-1-ethyl-3-(N,N,N',N'-tetramethylamidino)urea
1-(2'-ethyl-6'-chlorophenyl)-1-ethyl-3-(N,N-tetramethyleneamidino)urea
1-(2'-ethyl-6'-chlorophenyl)-1-ethyl-3-(N,N-tetramethylene-N'-methylamidino)urea
1-(2'-ethyl-6'-chlorophenyl)-1-propyl-3-methylamidinourea
1-(2'-ethyl-6'-chlorophenyl)-1-propyl-3-ethylamidinourea
1-(2'-ethyl-6'-chlorophenyl)-1-propyl-3-propylamidinourea
1-(2'-ethyl-6'-chlorophenyl)-1-propyl-3-i-propylamidinourea
1-(2'-ethyl-6'-chlorophenyl)-1-propyl-3-butylamidinourea
1-(2'-ethyl-6'-chlorophenyl)-1-propyl-3-i-butylamidinourea
1-(2'-ethyl-6'-chlorophenyl)-1-propyl-3-allylamidinourea
1-(2'-ethyl-6'-chlorophenyl)-1-propyl-3-propargylamidinourea
1-(2'-ethyl-6'-chlorophenyl)-1-propyl-3-(N,N-dimethylamidino)urea
1-(2'-ethyl-6'-chlorophenyl)-1-butyl-3-methylamidinourea
1-(2'-methyl-6'-fluorophenyl)-3-methylamidinourea
1-(2',6'-dimethyl-4'-hydroxyphenyl)-3-methylamidinourea
1-(2',6'-diethyl-4'-hydroxyphenyl)-3-methylamidinourea
1-(2'-methyl-6'-chloro-4'-hydroxyphenyl)-3-methylamidinourea
1-(2'-methyl-6'-bromo-4'-hydroxyphenyl)-3-methylamidinourea
1-(2'-methyl-6'-fluoro-4'-hydroxyphenyl)-3-methylamidinourea
1-(2'-methyl-6'-ethyl-4'-hydroxyphenyl)-3-methylamidinourea 1-(2'-ethyl-6'-chloro-4'-hydroxyphenyl)-3-methylamidinourea
1-(2'-ethyl-6'-bromo-4'-hydroxyphenyl)-3-methylamidinourea
1-(2'-ethyl-6'-fluoro-4'-hydroxyphenyl)-3-methylamidinourea
1-(2',6'-dimethyl-4'-aminophenyl)-3-methylamidinourea
1-(2',6'-diethyl-4'-aminophenyl)-3-methylamidinourea
1-(2'-methyl-6'-ethyl-4'-aminophenyl)-3-methylamidinourea
1-(2'-methyl-6'-chloro-4'-aminophenyl)-3-methylamidinourea
1-(2'-methyl-6'-bromo-4'-aminophenyl)-3-methylamidinourea
1-(2'-methyl-6'-fluoro-4'-aminophenyl)-3-methylamidinourea
1-(2'-ethyl-6'-chloro-4'-aminophenyl)-3-methylamidinourea
1-(2'-ethyl-6'-bromo-4'-aminophenyl)-3-methylamidinourea
1-(2'-ethyl-6'-fluoro-4'-aminophenyl)-3-methylamidinourea
1-(2',6'-dimethyl-4'-acetylamino)-3-methylamidinourea
1-(2',6'-diethyl-4'-acetylamino)-3-methylamidinourea
1-(2'-methyl-6'-ethyl-4'-acetylamino)-3-methylamidinourea
1-(2'-methyl-6'-chloro-4'-acetylamino)-3-methylamidinourea
1-(2'-methyl-6'-bromo-4'-acetylamino)-3-methylamidinourea
1-(2'-methyl-6'-fluoro-4'-acetylamino)-3-methylamidinourea
1-(2'-ethyl-6'-chloro-4'-acetylamino)-3-methylamidinourea
1-(2'-ethyl-6'-bromo-4'-acetylamino)-3-methylamidinourea
1-(2'-ethyl-6'-fluoro-4'-acetylamino)-3-methylamidinourea

EXAMPLE 8

A. A solution of 200 g. of 2,6-dimethylaniline in 2 l. of ether is cooled in an ice bath and to this 88 g. of butyryl chloride in 150 ml. of ether is added dropwise (over 2½ hours). A white precipitate forms and the reaction mixture is allowed to stir at 0° C. for 1 hour longer and then 15 hours at room temperature. The reaction mixture is then evaporated in vacuo and the white solid residue is slurried in 1 l. of water, filtered and washed with water and dried to obtain N-butyryl-2,6-dimethylaniline (m.p. 134°-6° C.).

B. A suspension of 148.7 g. of N-butyryl-2,6-dimethylaniline in 1200 ml. of THF, under nitrogen, is cooled to about −10° C. with ice/MeOH bath. With contant cooling and stirring, 1200 ml. of 0.99 M borane in THF is added dropwise over 4 hours maintaining the temperature about −5° C. After addition is complete, the mixture is allowed to warm to room temperature and then brought slowly to reflux and refluxed 6 hours followed by 15 hours at room temperature. The reaction mixture is then cooled in ice and 500 ml. of 6 NHCl added dropwise with stirring. The solution is then evaporated in vacuo and the volume of residue is brought to about 1 l. with water. This mixture is then cooled in ice and filtered. The aqueous portion is extracted three times with 500 ml. portions of ether, cooled in an ice bath and made alkaline with sodium hydroxide. The free base is extracted into ether with 3 × 400 ml. portions. The ether is dried over sodium sulfate, filtered, acidified with ethereal HCl and the resulting solid filtered and dried. This is then recrystallized from isopropanol (n-heptane) to give N-butyl-2,6-dimethylaniline hydrochloride (m.p. 124°-131° C.).

C. To a suspension of 31.5 g. of N-butyl-2,6-dimethylaniline in 400 ml. of toluene is added 50 ml. of phosgene. The solution is heated to reflux and refluxed for 30 minutes. The solvent is then allowed to distill off (ca 350 ml.) and then cooled. The solution is evaporated in vacuo to a light oil which is then dissolved into hexane, filtered and the hexane evaporated off in vacuo to give a milky oil which is then distilled to give 2,6-dimethyl-N-butylphenylcarbamoyl chloride (b.p. 105° C./0.1 mm)

When butyryl chloride in the above procedure is replaced by acetyl chloride, propionyl chloride isopropionyl chloride, isobutyryl chloride, t-butyryl chloride or pentanoyl chloride, then the products prepared are:
2,6-dimethyl-N-ethylphenylcarbamoyl chloride
2,6-dimethyl-N-propylphenylcarbamoyl chloride
2,6-dimethyl-N-isobutylphenylcarbamoyl chloride
2,6-dimethyl-N-pentylphenylcarbamoyl chloride When 2,6-dimethylphenyl-N-methyl-N-methylcarbamoyl chloride in Example 7D is replaced with the above carbamoyl chloride then the products prepared are
1-(2',6'-dimethylphenyl)-1-butyl-3-methylamidinourea nitrate
1-(2',6'-dimethylphenyl)-1-ethyl-3-methylamidinourea nitrate
1-(2',6'-dimethylphenyl)-1-propyl-3-methylamidinourea nitrate
1-(2',6'-dimethylphenyl)-1-i-propyl-3-methylamidinourea nitrate
1-(2',6'-dimethylphenyl)-1-i-butyl-3-methylamidinourea nitrate
1-(2',6'-dimethylphenyl)-1-t-butyl-3-methylamidinourea nitrate

EXAMPLE 9

1-(2,6-Diethyl-4-nitrophenyl)-3-methylamidinourea Hydrochloride

A. To a solution of 149.0 g (1.0 mole) of 2,6-diethylaniline in pyridine (500 ml) is added in portions at 0° C. 209.6 g (1.1 moles) of p-toluenesulfonyl chloride. The reaction mixture is allowed to come to room temperature and stir for three hours. The mixture is poured into cold aqueous 10% HCl and the crude sulfonamide solidified. The sulfonamide is filtered, washed with water and crystallized from acetic acid to give N-(2,6-diethylphenyl)-p-toluenesulfonamide m.p. 130°-131° C.

B. To a solution of 115 ml nitric acid (d=1.42) in water (900 ml) are added successively 129.9 g (0.43 moles) of N-(2,6-diethylphenyl)-p-toluenesulfonamide, glacial acetic acid (900 ml) and sodium nitrite (3.2 g). The mixture is boiled on a steam bath for 1.5 hours, then poured into ice water (2 l). The precipitate is filtered, washed with water and air-dried to give crude N-(2,6-diethyl-4-nitrophenyl)-p-toluenesulfonamide.

C. To 92.5 g (0.27 mole) of crude N-(2,6-diethylphenyl)-p-toluenesulfonamide is added 300 ml of a mixture of 300 ml of concentrated sulfuric acid and 30 ml of water and the mixture heated at 90° C. for fifteen minutes. After cooling, the mixture is poured into ice-water (2.5 l) and made basic with ammonia. The precipitated material is filtered and air-dried to give 2,6-diethyl-4-nitroaniline.

D. Excess phosgene is bubbled into a warm solution of 21.5 g (0.11 moles) of 2,6-diethyl-4-nitroaniline in toluene (250 ml). After the addition, the mixture is heated to reflux and approximately 200 ml of toluene are distilled. The remainder of the toluene is removed under vacuum and the remaining brown semi-solid is distilled under vacuum to give 2,6-diethyl-4-nitrophenylisocyanate, b.p. 135°–144° C./1 mm, as a yellow liquid which crystallized on standing.

E. To a stirred suspension of 7.3 g (30.0 mmol) of methylguanidine sulfate in tetrahydrofuran (80 ml) is added 4.8 g (60.0 mmol) of 50% w/w sodium hydroxide in water with continued stirring for one hour. Anhydrous sodium sulfate (10.0 g) is added and the mixture stirred an additional hour after which 6.6 g (30.0 mmol) of 2,6-diethyl-4-nitrophenylisocyanate is added and the resulting mixture stirred at room temperature overnight. The tetrahydrofuran is removed under vacuum and the residue partitioned between water and chloroform. The layers are separated and the aqueous layer extracted with chloroform (1 × 100 ml). The combined extracts are dried (MgSO$_4$) and concentrated to give a yellow foam which is dissolved in methanol and acidified with HCl/MeOH. The methanol is removed under vacuum to give a yellow viscous oil which solidifies on scratching. Crystallization from methanol-ethyl acetate gives 1-(2,6-diethyl-4-nitrophenyl)-3-methylamidinourea hydrochloride as a pale yellow solid, m.p. 173°–175° C.

When 2,6-diethylaniline in the above example is replaced by 2,6-dimethylaniline, 2-methyl-6-ethylaniline, 2-methyl-6-chloroaniline, 2-methyl-6-bromoaniline, 2-methyl-6-fluoroaniline, 2-ethyl-6-chloroaniline, 2-ethyl-6-bromoaniline and 2-ethyl-6-fluoroaniline, then the products prepared are
  1-(2,6-dimethyl-4-nitrophenyl)-3-methylanilineurea hydrochloride
  1-(2-methyl-6-ethyl-4-nitrophenyl)-3-methylanilineurea hydrochloride
  1-(2-methyl-6-chloro-4-nitrophenyl)-3-methylanilineurea hydrochloride
  1-(2-methyl-6-bromo-4-nitrophenyl)-3-methylanilineurea hydrochloride
  1-(2-methyl-6-fluoro-4-nitrophenyl)-3-methylanilineurea hydrochloride
  1-(2-ethyl-6-chloro-4-nitrophenyl)-3-methylanilineurea hydrochloride
  1-(2-ethyl-6-bromo-4-nitrophenyl)-3-methylanilineurea hydrochloride
  1-(2-ethyl-6-fluoro-4-nitrophenyl)-3-methylanilineurea hydrochloride When the various guanidines of Examples 1–4 are used in place of methylguanidine sulfate in the above example, then the corresponding product is obtained.

EXAMPLE 10

1-(4-amino-2,6-diethylphenyl)-3-methylamidinourea Dihydrochloride

A mixture of 5.0 g (15.2 mmol) of 1-(2,6-diethyl-4-nitrophenyl)-3-methylamidinourea hydrochloride and 5% paladium on carbon (500 mg) in absolute ethanol (175 ml) containing concentrated hydrochloric acid (2 ml) is shaken under an atmosphere of hydrogen (50 psi) for thirty minutes. The mixture is filtered through a Celite pad. To the filtrate is added HCl/MeOH and the alcohol is removed under vacuum to give a yellow foam which is crystallized from methanol-ethyl acetate to give 1-(4-amino-2,6-diethylphenyl)-3-methylamidinourea dihydrochloride, m.p. 218°–222° C. (dec).

When the nitro substituted amidinoureas of Example 9 are used in place of 1-(2,6-diethyl-4-nitrophenyl)-3-methylamidinourea hydrochloride, then the products prepared are:
  1-(2,6-dimethyl-4-aminophenyl)-3-methylamidinourea hydrochloride
  1-(2-methyl-6-ethyl-4-aminophenyl)-3-methylanilineurea hydrochloride
  1-(2-methyl-6-chloro-4-aminophenyl)-3-methylanilineurea hydrochloride
  1-(2-methyl-6-bromo-4-aminophenyl)-3-methylanilineurea hydrochloride
  1-(2-methyl-6-fluoro-4-aminophenyl)-3-methylanilineurea hydrochloride
  1-(2-ethyl-6-chloro-4-aminophenyl)-3-methylanilineurea hydrochloride
  1-(2-ethyl-6-bromo-4-aminophenyl)-3-methylanilineurea hydrochloride
  1-(2-ethyl-6-fluoro-4-aminophenyl)-3-methylanilineurea hydrochloride

EXAMPLE 11

1-Propargylguanidine Sulfate

To a vigorously stirred suspension of 50.11 g. (0.18 moles) of S-methylthiouronium sulfate in 100 ml. of water is added 20 g. (0.36 moles) of propargyl amine under a blanket of nitrogen. The reaction mixture is stirred at room temperature for 4 hours and then warmed slowly to reflux and refluxed for 2 hours. The heat is removed and the reaction mixture allowed to stir at room temperature for 2 days. The mixture is then heated to reflux, filtered and then evaporated to near dryness. The residual oil is triturated in isopropanol and the solid which separates is filtered and dried. This material is then resuspended in 1 l. of boiling methanol and water added dropwise until all of the solid dissolves. The solution is then cooled in an ice bath and the solid which separates is filtered, washed with methanol and dried to give 1-propargylguanidine sulfate (m.p. 200°–201° C.).

When allylamine is used in the above procedure in place of propargyl amine, then the product obtained is allylguanidine.

When benzyloxyethylamine is used in the above procedure in place of propargyl amine, then the product obtained is benzyloxyethylguanidine.

When propargylamine in the above procedure is replaced by any suitable amine, then the corresponding guanidine is prepared.

EXAMPLE 12

1-(2',6'-Dimethylphenyl)-3-methyl-3-methylamidinourea

A quantity of 20 g. of 1-(2',6'-dimethylphenyl)-3,5-dimethylbiguanide is added to 200 ml. of 10 hydrochloric acid and the mixture is refluxed for 3 hours. The reaction mixture is then filtered hot and then chilled. The material which separates is then filtered off and recrystallized from isopropanol/water to obtain 1-(2',6'-dimethylphenyl)-3-methyl-3-methylamidinourea hydrochloride.

The free base is prepared by dissolving the salt in 200 ml. of water and adding a 10% sodium hydroxide solution until alkaline. The reaction mixture is then extracted with chloroform which is dried and evaporated to dryness to obtain 1-(2',6'-dimethylphenyl)-3-methyl-3-methylamidinourea.

When the biguanides of Table I, below, are used in the above example in place of 1-(2',6'-dimethylphenyl)-3,5-dimethylbiguanide, then the corresponding product of Table II is obtained.

TABLE I 1-(2',6'-dimethylphenyl)-5-methylbiguanide
1-(2',6'-dimethylphenyl)-5,5-dimethylbiguanide
1-(2',6'-dimethylphenyl)-4,5-dimethylbiguanide
1-(2',6'-dimethylphenyl)-4,5,5-trimethylbiguanide
1-(2',6'-dimethylphenyl)-3-methylbiguanide
1-(2',6'-dimethylphenyl)-1-methylbiguanide
1-(2',6'-dimethylphenyl)-1,3-dimethylbiguanide
1-(2',6'-dimethylphenyl)-3,5-dimethylbiguanide
1-(2',6'-dimethylphenyl)-3,5,5-trimethylbiguanide
1-(2',6'-dimethylphenyl)-3,4,5-trimethylbiguanide
1-(2',6'-dimethylphenyl)-1,5-dimethylbiguanide
1-(2',6'-dimethylphenyl)-1,3,5-trimethylbiguanide
1-(2',6'-dimethylphenyl)-1,3,5,5-tetramethylbiguanide
1-(2',6'-dimethylphenyl)-1,3,4,5-tetramethylbiguanide
1-(2',6'-dimethylphenyl)-1,3,4,5,5-pentamethylbiguanide
1-(2',6'-diethylphenyl)-5-methylbiguanide
1-(2'-methyl-6'-methoxyphenyl)-5-methylbiguanide
1-(2'-methyl-6'-chlorophenyl)-5-methylbiguanide
1-(2'-methyl-6'-ethylphenyl)-5-methylbiguanide
1-(2'-methylphenyl)-5-methylbiguanide
1-(2',4',6'-trimethylphenyl)-5-methylbiguanide
1-(2'-methyl-4'-bromo-6'-chlorophenyl)-5-methylbiguanide
1-(2'-chloro-6'-fluorophenyl)-5-methylbiguanide
1-(2',5'-dichlorophenyl)-5-methylbiguanide
1-(2'-chloro-6'-bromophenyl)-5-methylbiguanide
1-(2'-chloro-5'-bromophenyl)-5-methylbiguanide
1-(2'-chloro-5'-fluorophenyl)-5-methylbiguanide
1-(2'-fluoro-5'-chlorophenyl)-5-methylbiguanide
1-(2'-fluoro-5'-bromophenyl)-5-methylbiguanide
1-(2',4',6'-triethylphenyl)-5-methylbiguanide
1-(2',4'-dimethyl-6'-ethylphenyl)-5-methylbiguanide
1-(2',6'-dimethyl-4'-ethylphenyl)-5-methylbiguanide
1-(2'-ethyl-6'-chlorophenyl)-5-methylbiguanide
1-(2'-ethylphenyl)-5-methylbiguanide
1-(2'-ethyl-4'-bromo-6'-chlorophenyl)-5-methylbiguanide
1-(2'-ethyl-6'-methoxyphenyl)-5-methylbiguanide
1-(2'-methyl-6'-ethoxyphenyl)-5-methylbiguanide
1-(2',6'-diethylphenyl)-3-methylbiguanide
1-(2'-methyl-6'-methoxyphenyl)-3-methylbiguanide
1-(2'-methyl-6'-chlorophenyl)-3-methylbiguanide
1-(2'-methyl-6'-ethylphenyl)-3-methylbiguanide
1-(2'-methylphenyl)-3-methylbiguanide
1-(2',4',6'-trimethylphenyl)-3-methylbiguanide
1-(2'-methyl-4'-bromo-6'-chlorophenyl)-3-methylbiguanide
1-(2'-chloro-6'-fluorophenyl)-3-methylbiguanide
1-(2',5'-dichlorophenyl)-3-methylbiguanide
1-(2',6'-dimethylphenyl)-5-ethylbiguanide
1-(2',6'-dimethylphenyl)-5-propylbiguanide
1-(2',6'-dimethylphenyl)-5-i-propylbiguanide
1-(2',6'-dimethylphenyl)-5-butylbiguanide
1-(2',6'-dimethylphenyl)-5-i-butylbiguanide
1-(2',6'-dimethylphenyl)-5-sec-butylbiguanide
1-(2',6'-dimethylphenyl)-5-t-butylbiguanide
1-(2',6'-dimethylphenyl)-5-pentylbiguanide
1-(2',6'-dimethylphenyl)-5-hexylbiguanide
1-(2',6'-dimethylphenyl)-5-heptylbiguanide
1-(2',6'-dimethylphenyl)-5-cyclopropylbiguanide
1-(2',6'-dimethylphenyl)-5-cyclobutylbiguanide
1-(2',6'-dimethylphenyl)-5-cyclopentylbiguanide
1-(2',6'-dimethylphenyl)-5-cyclohexylbiguanide
1-(2',6'-dimethylphenyl)-5-phenylbiguanide
1-(2',6'-dimethylphenyl)-5-benzylbiguanide
1-(2',6'-dimethylphenyl)-5-phenethylbiguanide
1-(2',6'-dimethylphenyl)-5,5-(N-methyl-3'-azapentamethylene)biguanide
1-(2',6'-dimethylphenyl)-5,5-(N-methyl-3'-azaheptamethylene)biguanide
1-(2',6'-dimethylphenyl)-5,5-(3'-oxopentamethylene)biguanide
1-(2',6'-dimethylphenyl)-5,5-(2'-thiatetramethylene)biguanide
1-(2',6'-dimethylphenyl)-5-methyl-5-ethylbiguanide
1-(2',6'-dimethylphenyl)-5,5-diethylbiguanide
1-(2',6'-dimethylphenyl)-5-methyl-5-benzylbiguanide
1-(2',6'-dimethylphenyl)-5,5-dibenzylbiguanide

TABLE II 3-(N-methylamidino)-1-(2,6-dimethylphenyl)urea
3-(N,N-dimethylamidino)-1-(2,6-dimethylphenyl)urea
3-(N,N'-dimethylamidino)-1-(2,6-dimethylphenyl)urea
3-(N,N,N'-trimethylamidino)-1-(2,6-dimethylphenyl)urea
3-methyl-3-amidino-1-(2,6-dimethylphenyl)urea
1-methyl-3-amidino-1-(2,6-dimethylphenyl)urea
1,3-dimethyl-3-amidino-1-(2,6-dimethylphenyl)urea
3-methyl-3-(N-methylamidino)-1-(2,6-dimethylphenyl)urea
3-methyl-3-(N,N-dimethylamidino)-1-(2,6-dimethylphenyl)urea
3-methyl-3-(N,N'-dimethylamidino)-1-(2',6'-dimethylphenyl)urea
1-methyl-3-(N-methylamidino)-1-(2',6'-dimethylphenyl)urea
1,3-dimethyl-3-(N-methylamidino)-1-(2',6'-dimethylphenyl)urea
1,3-dimethyl-3-(N,N-dimethylamidino)-1-(2',6'-dimethylphenyl)urea
1,3-dimethyl-3-(N,N'-dimethylamidino)-1-(2',6'-dimethylphenyl)urea
1,3-dimethyl-3-(N,N,N'-trimethylamidino)-1-(2',6'-dimethylphenyl)urea
3-(N-methylamidino)-1-(2',6'-diethylphenyl)urea
3-(N-methylamidino)-1-(2'-methyl-6'-methoxyphenyl)urea
3-(N-methylamidino)-1-(2'-methyl-6'-chlorophenyl)urea
3-(N-methylamidino)-1-(2'-methyl-6'-ethylphenyl)urea
3-(N-methylamidino)-1-(2'-methylphenyl)urea
3-(N-methylamidino)-1-(2',4',6'-trimethylphenyl)urea
3-(N-methylamidino)-1-(2'-methyl-4'-bromo-6'-chlorophenyl)urea
3-(N-methylamidino-)-1-(2'-chloro-6'-fluorophenyl)urea
3-(N-methylamidino)-1-(2',5'-dichlorophenyl)urea
3-(N-methylamidino)-1-(2'-chloro-6'-bromophenyl)urea
3-(N-methylamidino)-1-(2'-chloro-5'-bromophenyl)urea
3-(N-methylamidino)-1-(2'-chloro-5'-fluorophenyl)urea
3-(N-methylamidino)-1-(2'-fluoro-5'-chlorophenyl)urea
3-(N-methylamidino)-1-(2'-fluoro-5'-bromophenyl)urea
3-(N-methylamidino)-1-(2',4',6'-triethylphenyl)urea
3-(N-methylamidino)-1-(2',4'-dimethyl-6'-ethylphenyl)urea 3-(N-methylamidino)-1-(2',6'-dimethyl-4'-ethylphenyl-)urea
3-(N-methylamidino)-1-(2'-ethyl-6'-chlorophenyl)urea
3-(N-methylamidino)-1-(2'-ethylphenyl)urea
3-(N-methylamidino)-1-(2'-ethyl-4'-bromo-6'-chlorophenyl)urea
3-(N-methylamidino)-1-(2'-ethyl-6'-methoxyphenyl-)urea
3-(N-methylamidino)-1-(2'-methyl-6'-ethoxyphenyl-)urea
3-methyl-3-amidino-1-(2',6'-diethylphenyl)urea
3-methyl-3-amidino-1-(2-methyl-6-methoxyphenyl)urea
3-methyl-3-amidino-1-(2'-methyl-6'-chlorophenyl)urea
3-methyl-3-amidino-1-(2'-methyl-6'-ethylphenyl)urea
3-methyl-3-amidino-1-(2'-methylphenyl)urea
3-methyl-3-amidino-1-(2',4',6'-trimethylphenyl)urea
3-methyl-3-amidino-1-(2'-methyl-4'-bromo-6'-chlorophenyl)urea
3-methyl-3-amidino-1-(2'-chloro-6'-fluorophenyl)urea
3-methyl-3-amidino-1-(2',5'-dichlorophenyl)urea
3-(N-ethylamidino)-1-(2',6'-dimethylphenyl)urea
3-(N-propylamidino)-1-(2',6'-dimethylphenyl)urea
3-(N-i-propylamidino)-1-(2',6'-dimethylphenyl)urea
3-(N-butylamidino)-1-(2',6'-dimethylphenyl)urea
3-(N-i-butylamidino)-1-(2',6'-dimethylphenyl)urea
3-(N-sec-butylamidino)-1-(2',6'-dimethylphenyl)urea
3-(N-t-butylamidino)-1-(2',6'-dimethylphenyl)urea
3-(N-pentylamidino)-1-(2',6'-dimethylphenyl)urea
3-(N-hexylamidino)-1-(2',6'-dimethylphenyl)urea
3-(N-heptylamidino)-1-(2',6'-dimethylphenyl)urea
3-(N-cyclopropylamidino)-1-(2',6'-dimethylphenyl-)urea
3-(N-cyclobutylamidino)-1-(2',6'-dimethylphenyl)urea
3-(N-cyclopentylamidino)-1-(2',6'-dimethylphenyl)urea
3-(N-cyclohexylamidino)-1-(2',6'-dimethylphenyl)urea
3-(N-phenylamidino)-1-(2',6'-dimethylphenyl)urea
3-(N-benzylamidino)-1-(2',6'-dimethylphenyl)urea
3-(N-phenethylamidino)-1-(2',6'-dimethylphenyl)urea
3-(N,N-pentamethyleneamidino)-1-(2',6'-dimethylphenyl)urea
3-[N,N-(N-methyl-3'-azapentamethylene)amidino]-1-(2',6'-dimethylphenyl)urea
3-[N,N-(N-methyl-3'-azaheptamethylene)amidino]-1-(2',6'-dimethylphenyl)urea
3-[N,N-(3'-oxopentamethylene)amidino]-1-(2',6'-dimethylphenyl)urea
3-[N,N-(2'-thiatetramethylene)amidino]-1-(2',6'-dimethylphenyl)urea
3-(N-methyl-N-ethylamidino)-1-(2',6'-dimethylphenyl-)urea
3-(N,N-diethylamidino)-1-(2',6'-dimethylphenyl)urea
3-(N-methyl-N-benzylamidino-1-(2',6'-dimethylphenyl-)urea
3-(N,N-dibenzylamidino)-1-(2',6'-dimethylphenyl)urea

EXAMPLE 13

Ten thousand tablets for oral use, each containing 50 mg. of 1-(2',6'-dichlorophenyl)-3-methylamidinourea hydrochloride, are prepared from the following types and amounts of material:

| Ingredient: | Grams |
|---|---|
| 1 - (2',6'-dichlorophenyl)-3-methylamidinourea hydrochloride | 500 |
| Lactose U.S.P. | 350 |
| Potato Starch U.S.P. | 346 |

The mixture is moistened with an alcoholic solution of 20 grams of stearic acid and granulated through a sieve. After drying, the following ingredients are added:

| Ingredient: | Grams |
|---|---|
| Potato Starch U.S.P. | 320 |
| Talcum | 400 |
| Magnesium stearate | 500 |
| Golloidal silicium dioxide | 64 |

The mixture is thoroughly mixed and compressed into tablets.

EXAMPLE 14

Five hundred ampoules each with two ml. of solution which contain 15 mg. of 1-(2-methyl-6-chlorophenyl)-3-methylamidinourea hydrochloride is prepared from the following types and amounts of materials:

| Ingredient: | Grams |
|---|---|
| 1 - (2-methyl)-6-chlorophenyl)-3-methyl-amidinourea hydrochloride | 7.5 |
| Ascorbic acid | 1 |
| Sodium bisulphite | 0.5 |
| Sodium sulphite | 1 |

EXAMPLE 15

Capsules are prepared as follows:
15 g. of 1-(2,6-diethylphenyl)-3-methylamidinourea hydrochloride,
3 g. magnesium stearate,
2 g. of finely divided silica sold under the trademark CAB-O-SIL by Godfrey L. Cabot, Inc., Boston, Mass.,
and
369 g. of lactose.

The ingredients are thoroughly mixed with each other and the mixture is filled in gelatin capsules. Each capsule contains 500 mg. of the composition and thus 15 mg. of 1-(2,6-diethylphenyl)-3-methylamidinourea hydrochloride.

EXAMPLE 16

50 g. of 1-(2',6'-dimethylphenyl)-3-methylamidinourea hydrochloride, 5 g. of propyl p-hydroxybenzoate are dissolved and dilluted to 5000 cc. with twice distilled water after the addition of modified Sorensen buffer solution in an amount sufficient to adjust the pH-value to a pH of 6.0. Sodium chloride is dissolved therein in an amount sufficient to render the resulting solution isotonic. The final solution is passed through a bacteriological filter and the filtrate is autoclaved at 120 C. for 15 minutes to yield a parenterally applicable solution which contains 50 mg. of 1-(2',6'-dimethylphenyl)-3-methylamidinourea hydrochloride in 5 cc.

We claim:
1. A method for producing local anesthetic action in a patient which comprises administering parenterally to said patient an effective daily dosage of between 0.1 and 70 mg/kg of body weight of said patient a compound of the formula:

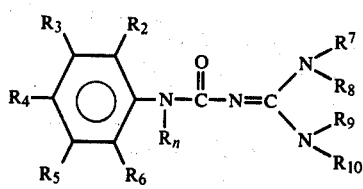

where:
R$_2$, R$_3$, R$_4$, R$_5$ and R$_6$ may be the same or different and are:
hydrogen,
halo,
loweralkyl,
haloloweralkyl,
nitro,
amino,
acylamino or
loweralkoxy;
R$_n$ is hydrogen or
loweralkyl; and
R$_7$, R$_8$, R$_9$ and R$_{10}$ are:
hydrogen,
alkyl,
alkenyl,
alkynyl,
cycloalkyl,
cycloalkenyl,
cycloalkylloweralkyl,
alkoxyloweralkyl,
aralkoxyloweralkyl or
aralkyl;
and the non-toxic acid addition salts thereof.

2. The method of claim 1 where:
R$_2$ is hydrogen, methyl or ethyl;
R$_3$ and R$_5$ are hydrogen;
R$_4$ is hydrogen, methyl, ethyl, chloro or bromo;
R$_6$ is hydrogen,
methyl,
ethyl,
nitro,
methoxy,
ethoxy,
chloro,
bromo or
fluoro;
R$_n$ is hydrogen,
methyl or ethyl, and
R$_7$, R$_8$, R$_9$ and R$_{10}$ are hydrogen,
methyl,
ethyl,
propyl,
i-propyl,
butyl,
i-butyl,
sec-butyl,
t-butyl,
pentyl,
hexyl,
heptyl,
allyl,
propargyl,
methoxyethyl,
ethoxyethyl,
benzyloxyethyl; provided R$_7$, R$_8$, R$_9$ and R$_{10}$ are not all hydrogen at the same time.

3. The method of claim 2 where:
R$_2$ and R$_6$ are diloweralkyl; R$_n$, R$_3$, R$_4$, R$_5$, R$_8$, R$_9$ and R$_{10}$ are hydrogen and R$_7$ is loweralkyl.

4. The method of claim 3 where:
R$_2$, R$_6$ and R$_7$ are methyl.

5. The method of claim 3 where:
R$_2$ and R$_6$ are ethyl and R$_7$ is methyl.

6. A method for producing local anesthetic action in a patient which comprises administering topically to said patient a composition containing, in the range of 0.1–10% by weight of said composition, a compound of the formula:

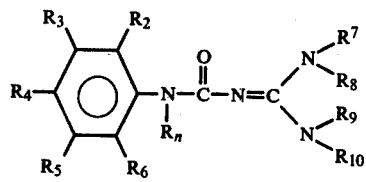

where:
R$_2$, R$_3$, R$_4$, R$_5$ and R$_6$ may be the same or different and are:
hydrogen,
halo,
loweralkyl,
haloloweralkyl,
nitro,
amino,
acylamino or
loweralkoxy
R$_n$ is hydrogen or
loweralkyl; and
R$_7$, R$_8$, R$_9$ and R$_{10}$ are:
hydrogen,
alkyl,
alkenyl,
alkynyl,
cycloalkyl,
cycloalkenyl,
cycloalkylloweralkyl,
alkoxyloweralkyl,
aralkoxyloweralkyl or
aralkyl;
and the non-toxic acid addition salts thereof.

7. The method of claim 6 where:
R$_2$ is hydrogen, methyl or ethyl;
R$_3$ and R$_5$ are hydrogen;
R$_4$ is hydrogen, methyl, ethyl, chloro or bromo;
R$_6$ is hydrogen;
methyl,
ethyl,
nitro,
methoxy,
ethoxy,
chloro,
bromo or
fluoro;
R$_n$ is hydrogen,
methyl or ethyl, and
R$_7$, R$_8$, R$_9$ and R$_{10}$ are hydrogen
methyl,
ethyl,
propyl,
i-propyl,
butyl,
i-butyl,
sec-butyl, t-butyl,
pentyl,
hexyl,
heptyl,
allyl,
propargyl,
methoxyethyl,
ethoxyethyl, or benzyloxyethyl; provided $R_7$, $R_8$, $R_9$ and $R_{10}$ are not all hydrogen at the same time.

8. The method of claim 7 where:
$R_2$ and $R_6$ are diloweralkyl; $R_n$, $R_3$, $R_4$, $R_5$, $R_8$, $R_9$ and $R_{10}$ are hydrogen and $R_7$ is loweralkyl.

9. The method of claim 8 where:
$R_2$, $R_6$ and $R_7$ are methyl.

10. The method of claim 8 where:
$R_2$ and $R_6$ are ethyl and $R_7$ is methyl.

* * * * *